US007038588B2

(12) United States Patent
Boone et al.

(10) Patent No.: US 7,038,588 B2
(45) Date of Patent: May 2, 2006

(54) APPARATUS AND METHOD FOR PATIENT POINT-OF-CARE DATA MANAGEMENT

(75) Inventors: Otho N. Boone, Ambler, PA (US); Nancy St. Clair, Malvern, PA (US); John H. Richards, Warrington, PA (US); Ian McDermott, Lincoln University, PA (US); Joseph P. Bagnell, Southampton, PA (US); Robert J. Strecker, Philadelphia, PA (US)

(73) Assignee: Draeger Medical Infant Care, Inc., Telford, PA (US)

( * ) Notice: Subject to any disclaimer, the term of this patent is extended or adjusted under 35 U.S.C. 154(b) by 335 days.

(21) Appl. No.: 10/146,076

(22) Filed: May 15, 2002

(65) Prior Publication Data

US 2002/0196141 A1 Dec. 26, 2002

Related U.S. Application Data

(63) Continuation-in-part of application No. 09/849,580, filed on May 4, 2001.

(60) Provisional application No. 60/327,496, filed on Oct. 5, 2001, provisional application No. 60/291,043, filed on May 15, 2001.

(51) Int. Cl.
*G08B 23/00* (2006.01)
(52) U.S. Cl. .............................. 340/573.1; 340/691.6; 340/693.6; 5/600; 5/655; 600/22; 600/300; 600/523; 705/3; 348/159
(58) Field of Classification Search ............. 340/573.1, 340/693.5, 691.6; 5/600, 655; 600/22, 300, 600/523; 705/3

See application file for complete search history.

(56) References Cited

U.S. PATENT DOCUMENTS

| 2,663,608 | A | | 12/1953 | Schauer |
| 3,470,866 | A | | 10/1969 | Gittelson |
| 4,216,462 | A | | 8/1980 | McGrath et al. |
| 4,356,475 | A | | 10/1982 | Neumann et al. |
| 4,958,645 | A | | 9/1990 | Cadell et al. |
| 5,038,800 | A | | 8/1991 | Oba |
| 5,308,310 | A | | 5/1994 | Roff et al. |
| 5,396,347 | A | * | 3/1995 | Kaneko ...................... 358/448 |
| 5,417,222 | A | | 5/1995 | Dempsey et al. |
| 5,441,047 | A | | 8/1995 | David et al. |
| 5,446,934 | A | | 9/1995 | Frazier |
| 5,447,164 | A | * | 9/1995 | Shaya et al. ................ 600/523 |
| 5,473,536 | A | | 12/1995 | Wimmer |

(Continued)

FOREIGN PATENT DOCUMENTS

DE       7334435       1/1974

(Continued)

*Primary Examiner*—Benjamin C. Lee
(74) *Attorney, Agent, or Firm*—Caesar, Rivise, Bernstein, Cohen & Pokotilow, Ltd.

(57) ABSTRACT

An apparatus and method for patient point-of-care data management is provided. Patient point-of-care data is obtained in realtime or in substantially realtime and is made available to subscribers or authorized users on either a local computer display screen, a remote computer display screen, or both. In some embodiments, data associated with a plurality of patients is made available and is viewable simultaneously on a computer display screen. In some embodiments, patient point-of-care data from a plurality of hospitals is available.

21 Claims, 24 Drawing Sheets

U.S. PATENT DOCUMENTS

| | | |
|---|---|---|
| 5,544,649 A | 8/1996 | David et al. |
| 5,579,775 A | 12/1996 | Dempsey et al. |
| 5,664,270 A * | 9/1997 | Bell et al. ................... 5/600 |
| 5,687,717 A | 11/1997 | Halpern et al. |
| 5,732,401 A * | 3/1998 | Conway ..................... 705/29 |
| 5,752,917 A | 5/1998 | Fuchs |
| 5,833,623 A * | 11/1998 | Mann et al. ............... 600/523 |
| 5,867,821 A | 2/1999 | Ballantyne et al. |
| 5,889,568 A | 3/1999 | Seraphim et al. |
| 5,894,322 A * | 4/1999 | Hamano et al. ............ 348/68 |
| 5,907,291 A | 5/1999 | Chen et al. |
| 5,944,659 A | 8/1999 | Flach et al. |
| 5,950,630 A | 9/1999 | Portwood et al. |
| 5,987,519 A | 11/1999 | Peifer et al. |
| 6,074,345 A | 6/2000 | van Oostrom et al. |
| 6,101,478 A | 8/2000 | Brown |
| 6,104,443 A * | 8/2000 | Adcock et al. ............ 348/827 |
| 6,125,350 A | 9/2000 | Dirbas |
| 6,168,563 B1 | 1/2001 | Brown |
| 6,210,320 B1 | 4/2001 | Rogone et al. |
| 6,296,606 B1 | 10/2001 | Goldberg et al. |
| 6,322,502 B1 | 11/2001 | Schoenberg et al. |
| 6,345,402 B1 | 2/2002 | Prows et al. |
| 6,367,476 B1 | 4/2002 | Conn |
| 6,375,017 B1 | 4/2002 | Schattner et al. |
| 6,409,654 B1 | 6/2002 | McClain |
| 6,487,735 B1 * | 12/2002 | Jacques et al. ................. 5/424 |
| 6,679,830 B1 * | 1/2004 | Kolarovic et al. ........... 600/22 |
| 2001/0035702 A1 | 11/2001 | Murphy et al. |
| 2001/0056226 A1 | 12/2001 | Zodnik et al. |
| 2002/0065685 A1 | 5/2002 | Monteleone et al. |

FOREIGN PATENT DOCUMENTS

| | | |
|---|---|---|
| DE | 2433882 | 2/1976 |
| DE | 3205097 | 10/1982 |
| DE | 3915882 | 11/1990 |
| DE | 4228873 | 10/1993 |
| DE | 29709848 | 8/1997 |
| WO | WO 94/13198 | 6/1994 |
| WO | WO 97/12474 | 4/1997 |
| WO | WO 98/02107 | 1/1998 |
| WO | WO 98/29775 | 7/1998 |
| WO | WO 99/12511 | 3/1999 |
| WO | WO 00/69387 | 11/2000 |
| WO | WO 01/86575 A2 | 11/2001 |

* cited by examiner

USER: DR. SMYTHE, JANE
TIME: 9:49 AM 11.1.01

MAIN DISPLAY CONTROL

MODE    CONTENT
SINGLE  MULTI

— 228
— 230

| | TRACE | SETUP | VIDEO | SUPPLIES |
|---|---|---|---|---|
| | VIDEO CONF. | E-MAIL | WEB | SCHEDULE |
| | HILL-ROM | RESEARCH | ASSESS-MENT | EDUCATION |
| | PUMPS/FLUIDS | MEDICA-TIONS | | |
| | RADIO-LOGY | LABS | TALK | |
| | LOG-OUT | | MAIN | |

— 328
— 232

L1 HR: 153 BPM
ABP: 53/41 MMHG
VBP: 9 MMHG
RR: 52 BPM
SpO2: 96%

— 196
— 480
— 198

MEDICATIONS FOR: 486 JONES, KEVIN_5367388 4901355 GM

| DRUG | SUPPLIED | DOSE/KG | DOSE(MG) | DOSE(ML) |
|---|---|---|---|---|
| ATROPINE | 0.1 MG/ML | 0.01 MG | 0.01355 | 0.1355 |
| NAHCO3 | 0.5 MEG/ML | 2 MEQ | 2.71 | 5.42 |
| CA GLUCOMATE | 100 MG/ML | 30 MG | 40.65 | 0.4065 |
| DEXTROSE, 10% | 1 MG/ML | 2 ML | 2.71 | 2.71 |
| EPINEPHRINE 1:10,000 | 1 MG/ML | 0.1 MG | 0.1355 | 0.1355 |
| LASIX | 10 MG/ML | 1 MG | 0.355 | 0.1355 |
| LIDOCAINE 2% | 20 MG/ML | 1 MG | 0.355 | 0.06775 |

CHANGE WEIGHT  EDIT NEEDS  GET INFO  DETAILS  MESSAGE
— 494  — 496  — 498  — 500

BED | ARM | ANGLE
— 210

FIG. 23

NAME: JONES, KEVIN
BED: 48    ALARM
AGE: 12 DAYS
LAST WT: 1335 GM @ 9.13.01
BIRTH WT: 1680 GM
PHYSN: DR. J. SMYTHE
NURSE: P. PURCELL

— 188
— 190
— 192

TAIR: 34°C
TBABY: 36.6/37.1°C
RH: 61 %
O2: -

FIO2: 26 %
RR: 53 BPM
PIP: 14 MMH2O
CPAP: 2.5 MMH2O
I:E: 0.2:0.3
PEEP: 3.0 MMH2O

— 194

APPARATUS AND METHOD FOR PATIENT POINT-OF-CARE DATA MANAGEMENT

This application claims priority under 35 U.S.C. § 119(e) to U.S. Provisional Patent Application Ser. No. 60/291,043, filed on May 15, 2001, and to U.S. Provisional Patent Application Ser. No. 60/327,496, filed on Oct. 5, 2001; and this application is also a continuation-in-part of U.S. Patent Application Ser. No. 09/849,580, filed on May 4, 2001; the disclosures of each of these applications being hereby incorporated by reference herein.

BACKGROUND AND SUMMARY

The present disclosure relates generally to a healthcare data system, and particularly, to an apparatus and method for collecting and distributing patient point-of-care data. More particularly, the present disclosure relates to a method and apparatus of patient point-of-care data management.

Data systems have been developed which provide information to various groups within the healthcare industry. Specifically, such data systems include systems that collect, process, and store certain information relating to patients. For example, data systems for use in the health insurance industry have been developed for the purpose of collecting, storing, and processing patient information such as demographic information, diagnosis information, and treatment information. Such information is sometimes used by an insurance provider in order to pay and track payments made on behalf of the patient as part of the patient's benefit plan.

It is known that hospitals may also maintain data systems for use in providing patient care within the hospital itself (as opposed to providing the data to an outside party such as an insurance company). In regard to such data systems, the hospital may maintain a database that includes information associated with individual patients and the care provided by the hospital.

Many conventional data collection and management systems used in the healthcare environment do not provide for the collection, storage, and processing of realtime or near-realtime patient point-of-care data across a large number of hospitals or across a patient population within a single hospital. In particular, while certain insurance systems may be useful for collecting and maintaining patient treatment data, such systems do not include the capability to collect patient "point-of-care data," which in this disclosure includes sensory data from sensors associated with the patient and device data from the devices being utilized to care for the patient. For example, sensory data (e.g., heart rate, blood pressure, breath rate, temperature, or other forms of sensed data) and device data (e.g., air temperature within an infant incubator) are typically not utilized by the insurance company, and therefore, are not collected by the data systems employed by the insurance companies. Moreover, while certain hospital data systems have been useful in collecting certain types of sensory data, such systems have been designed for use only within a single hospital and, as a result, do not include information relating to patients at other hospitals.

According to this disclosure, a data collection and management system is configured to permit authorized users or subscribers to access online, realtime or near-realtime patient point-of-care data. In some disclosed embodiments, the patient point-of-care data is collected from patients and/or devices located at a plurality of healthcare facilities. In other disclosed embodiments, the point-of-care data is collected from a plurality of patients and/or devices located in a single healthcare facility. In those embodiments in which point-of-care data is collected from a plurality of healthcare facilities, the system includes a central database in which the point-of-care data from each facility is stored. In some embodiments, the system is configured to permit access to the database of point-of-care data via the Internet.

Further according to this disclosure, a method for providing sensed patient data to subscribers comprises providing a database for collecting online patient point-of-care data from a plurality of patients in a plurality of hospitals. Each of the patients and each of the hospitals is identified by a respective identification code. The method includes collecting and sorting the sensed patient data. The method further includes permitting subscribers online access to the database of point-of-care data.

Additionally, according to this disclosure, a method of operating a healthcare data system comprises receiving patient point-of-care data associated with a plurality of patients located in a plurality of hospitals and storing the received patient point-of-care data in a database. Some of the patient point-of-care data is generated by a plurality of sensors, each of which senses at least one physical characteristic associated with a respective patient. In some embodiments, the method further comprises entering at least a portion of the patient point-of-care data into the database. The method further comprises retrieving at least some of the point-of-care data from the database upon receipt of a request from a subscriber. The method also includes the step of transmitting the sensed patient data to the subscriber.

According to this disclosure, a healthcare data system comprises a communication device for transmitting and receiving patient point-of-care data, a storage device for maintaining a patient database, and a processing unit electrically coupled to both the communication device and the storage device. The healthcare data system also includes a memory device electrically coupled to the processing unit. The memory device has stored therein a plurality of operating instructions which, when executed by the processing unit, causes the processing unit to operate the communication device to receive patient point-of-care data associated with a plurality of patients located in a plurality of hospitals. Some of the sensed patient point-of-care data is generated by a plurality of sensors, each of which senses a physical characteristic associated with a respective patient. The plurality of instructions, when executed by the processing unit, further causes the processing unit to enter the patient point-of-care data into a database. The plurality of instructions, when executed by the processing unit, also causes the processing unit to retrieve at least some of the patient point-of-care data from the database upon receipt of a request from a subscriber. Furthermore, the plurality of instructions, when executed by the processing unit, causes the processing unit to operate the communication device to transmit the retrieved patient point-of-care data to the subscriber.

Further according to this disclosure, a patient care device for use in a healthcare facility having a network of computer devices is provided. The patient care device comprises a support structure, a computer coupled to the support structure, and a mattress supported by the support structure. The mattress having a surface on which a patient lies. The computer receives patient point-of-care data, including data representative of at least one vital sign of the patient. The computer is coupled to the network and sends the patient point-of-care data to at least one of the computer devices of the network.

Also according to this disclosure, a patient care device has a support structure, a mattress supported by the support structure, a computer coupled to the support structure, and a camera coupled to the support structure. The computer has a display screen. An image from the camera is shown on a first portion of the display screen and patient point-of-care data is shown on a second portion of the display screen.

In some embodiments, the image from the camera is accessible via the Internet for viewing on a display screen of a remote computer. In other embodiments, the computer is configured to permit the image from the camera to be e-mailed to an e-mail address. In the illustrative embodiment, any one or more of the following types of additional data is shown on other portions of the display screen when the appropriate commands are received by the computer: environmental data, such as temperature or humidity, associated with a patient space around the mattress; patient biographical data; a stored radiographic image of the patient; a stored ultrasound image of the patient; stored laboratory test results; a recorded video message; controls for listening to a recorded audio message; controls for sending an e-mail; controls for conducting a videoconference; controls for browsing the Internet; data related to manufacturer sales or service; a list of supplies associated with the care of the patient; a schedule of medical appointments of the patient; medication data, including dosage data; and point-of-care data of one or more other patients supported on other patient care devices. Any or all of these other types of data may be used to populate the central database to which authorized users or subscribers have access online.

According to this disclosure, a patient care system comprises a patient support device having a surface on which a patient lies and a computer associated with the patient support device. The computer has a reader and a display. In addition, the computer is configured to store patient point-of-care data. The patient point-of-care data includes a first subset of patient point-of-care data and a second subset of patient point-of-care data. The patient care system further comprises a first token and a second token. The computer is configured to grant access to the first subset of patient point-of-care data if the first token is presented to the reader and the computer is configured to grant access to the second subset of patient point-of-care data if the second token is presented to the reader.

In an illustrative embodiment, the patient care device is an infant thermal support device which is operable either as an infant incubator or as a radiant warmer. The illustrative infant thermal support device has a vertical column to which a canopy and a radiant heater are coupled. The column is extendable and retractable to raise and lower the canopy and the radiant warmer. An arm assembly is coupled to a lower portion of the column and is pivotable about a vertical axis. The computer is coupled to an end of the arm assembly such that the computer is spaced apart from the column. The arm assembly includes a plurality of arm segments that are configured to permit movement of the computer about the column from a first side of the infant thermal support device to a second side of the thermal support device.

Additional features will become apparent to those skilled in the art upon consideration of the following detailed description of illustrative embodiments exemplifying the best mode of carrying out the method and apparatus for patient point-of-care data management as presently perceived.

BRIEF DESCRIPTION OF THE DRAWINGS

The detailed description particularly refers to the accompanying figures, in which:

FIG. 2 is a table showing a number of exemplary data fields which may be populated with data during operation of the system of FIG. 1;

FIG. 12 is an example of a screen printout of a Video Message screen that appears on the display screen when a Video Message icon is selected on the Message screen of FIG. 11;

FIG. 22 is an example of a screen printout of a Radiology screen that appears on the display screen when a Radiology icon is selected from the main menu;

FIG. 23 is an example of a screen printout of a Medications screen that appears on the display screen when a Medications icon is selected from the main menu;

DETAILED DESCRIPTION OF THE DRAWINGS

Figure 1:
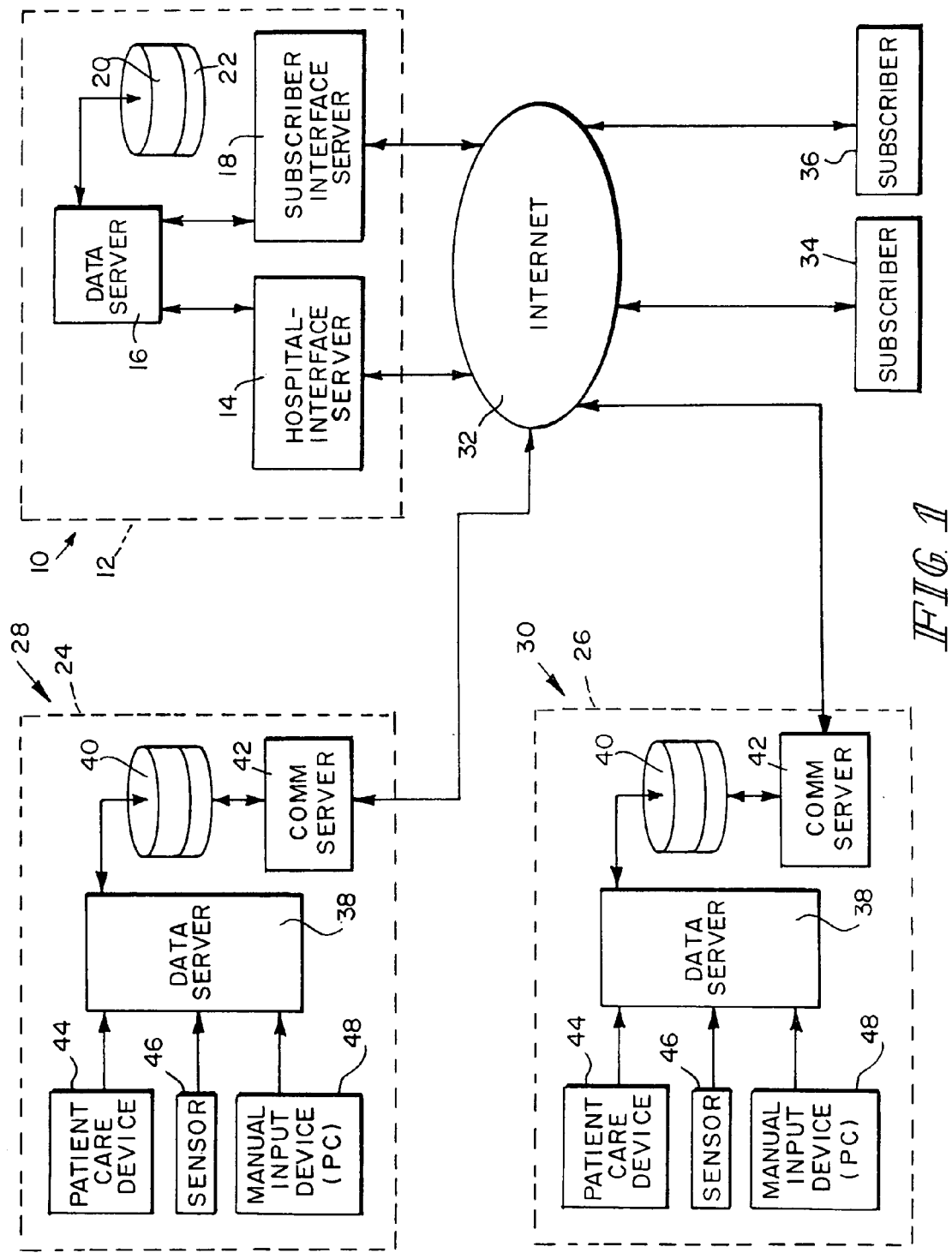
FIG. 1 is a block diagram of a patient point-of-care data collection and distribution system according to this disclosure showing a repository network having a hospital-interface server and a subscriber-interface server, the repository network being coupled to the Internet, a plurality of hospital computer systems coupled to the Internet, each hospital computer system having a data server and a plurality of patient point-of-care data collection devices coupled to the respective data server, and a plurality of subscribers coupled to the Internet to access patient point-of-care data.

Referring now to FIG. 1, there is shown one exemplary embodiment of a patient point-of-care data system 10 which includes a repository network 12 having a number of servers such as a hospital-interface server 14, an internal data server 16, and a subscriber-interface server 18. As discussed below in greater detail, hospital-interface server 14 communicates with a number of different hospital networks 24, 26 which are respectively associated with a number of different hospitals 28, 30 in order to accumulate patient point-of-care data associated with the numerous patients being treated in the hospitals 28, 30. The terms "hospital," "healthcare facility," and "facility" as used in this disclosure, including in the claims, are each intended to cover all types of facilities at which healthcare is provided, including hospitals, nursing homes, outpatient surgery centers, doctor's offices, rehabilitation centers, and the like. As also discussed below in greater detail, subscriber-interface server 18 communicates with a number of authorized users or subscribers 34, 36. Although only two hospitals 28, 30 and two subscribers 34, 36 are shown in FIG. 1 for purposes of brevity, it is within the scope of this disclosure for repository network 12 to exchange data with any number of hospital networks associated with any number of hospitals, along with any number of subscribers.

Each of the servers 14, 16, 18 may be configured as either individual hardware or software components. Specifically, each of the servers 14, 16, 18 may be embodied as an individual (i.e., separate) hardware device having components such as a processing unit (not shown) including the associated memory devices (e.g., RAM modules, hard drives, or other type of storage device), along with other commonly utilized hardware components such as a high band width data router or the like. Alternatively, the servers 14, 16, 18 may be embodied as individual software components, each of which is operated on a common piece of server hardware similar to as described above. Any combination of the above configurations is within the scope of the present disclosure.

In one exemplary embodiment, the individual hospital networks 24, 26 communicate with the repository network 12 via any type of network which is capable of interconnecting the networks 12, 24, 26. For example, the network utilized to allow for communication between the individual hospital networks 24, 26 and the repository network 12 may be a global network such as the internet 32. It should be appreciated that although a specific configuration of a network is described herein and shown in the drawings (i.e., the Internet 32), other network configurations are also contemplated for use in accordance with this disclosure. For example, the network may be embodied as other global networks or, alternatively, as proprietary networks such as a wide area network (WAN).

The individual subscribers 34, 36 may also communicate with the repository network 12 via a similar network configuration. Hence, in the exemplary embodiment described herein and shown in the drawings, the individual subscribers 34, 36 may also communicate with the repository network 12 via the internet 32. However, similarly to as discussed above, other network configurations such as other global networks or proprietary WAN's are also contemplated for use to allow the individual subscribers 34, 36 to communicate with the repository network 12.

The repository network 12 also includes a number of storage devices 20. The storage devices 20 are utilized in order to maintain a number of patient databases 22. Specifically, the repository network 12 communicates with the hospital networks 24, 26 (via use of the hospital-interface server 14) in order to accumulate data associated with the patients hospitalized within each of the hospitals 28, 30. Such data is maintained in the patient databases 22 for use by the subscribers 34, 36. In such a configuration, the data server 16 controls the movement of information into and out of the databases 22.

As shall be described in greater detail below, the afore-described configuration of the data system 10 allows for realtime or near-realtime accumulation of patient data from a relatively large number of hospitals. Such accumulated data may then be made selectively available to a large number of subscribers 34, 36 for use for such purposes as clinical research, routine treatment, or the like.

Each of the hospital networks includes an internal data server 38, a storage device 40, and an external communications server 42. The internal data server 38 communicates with a number of devices utilized in the hospitals 28, 30 in order to receive patient care data therefrom for storage in a number of databases maintained by the storage device 40. In particular, each of the hospitals 24, 26 utilizes a number of patient-care devices 44 in order to provide the necessary care to a patient. The patient-care device may take the form of any type of device which is utilized in a hospital or similar care facility for rendering care to a patient. For example, the patient-care devices 44 may take the form of an infant incubator, heart-lung machine, EKG, ECG, MRI, X-ray, blood fluid analysis device, or any other type of device which is commonly utilized to provide care to a patient.

In an illustrative embodiment of a patient care device 44', which is described in further detail below with reference to FIGS. 5–25, the device 44' takes the form of an incubator and warmer device of the type described in U.S. Pat. Nos. 5,453,077; 5,817,002; 5,817,003; 5,759,149; 5,971,913; 5,971,914; 6,022,310; 6,024,694; 6,036,634; 6,049,924; 6,071,228; 6,270,452; 6,296,606; and 6,345,402; and in U.S. patent application Ser. Nos. 09/688,528 filed on Oct. 16, 2000; 09/571,449 filed on May 16, 2000; 09/838,789 filed on Apr. 20, 2001; and 10/027,496 filed on Dec. 21, 2001. Each of the patents and patent applications listed in the preceding sentence are hereby incorporated by reference herein. As such, the patient-care device 44' (e.g., the infant incubator) includes a number of sensors or the like (not shown) for collecting data associated with operation thereof (hereinafter "device data"). For example, the patient-care device 44' may include sensors for determining the air temperature within the device, the rate at which any intravenous medications are being administered, the oxygen content of the air within the device, the weight of the patient, and/or the air circulation rate within the device.

Moreover, a number of other patient sensors 46 are also utilized to collect data associated with the patient (hereinafter "sensor data"). For example, sensors may be utilized to determine the skin and/or internal temperature of the patient, the patient's heart and/or respiratory rate, the oxygen level in the patient's blood, the patient's blood pressure, and/or the patient's fluid discharge level. It should be appreciated that a number of the sensors 46 may be integrated into the patient-care devices 44. For example, in the case of an infant incubator, the temperature sensor for monitoring the skin temperature of the patient may be integrated into the incubator. As such, certain types of "sensor data" may also be characterized as "device data".

Patient data may also be input manually (hereinafter "manual data") via use of a number of manual input devices such as personal computers (PC's) 48. Manual data may take the form of a patient code such as a patient identification number. Manual data may also take the form of demographic information such as age, sex, race along with other information relating to the patient which is commonly collected at the time the patient is admitted to the hospital such as the patient's height and weight and the like. In addition to information collected at the time of admission to the hospital, manual data may also take the form of information collected at the time of patient discharge from the hospital or transfer to another facility. If the patient was monitored by a home monitoring system prior to admission to the hospital, information collected by such a home monitoring system may also be manually entered (or alternatively, may be entered directly by the home monitoring system if it is in communication with the hospital's network).

Moreover, diagnostic data such as diagnostic codes may be manually entered via use of the PC's 48 in order to identify the ailments or conditions for which the patient is being treated. Similarly, treatment data such as treatment codes may also be manually entered via use of the PC's 48 in order to identify the procedures and/or medications which are being utilized in the treatment of the patient. It should be appreciated that the diagnostic codes and treatment codes may be provided in a universally accepted format such as Medicare (federal) and insurance codes or any other type of code which is commonly utilized in the healthcare industry.

The patient data described above is communicated to the hospital's internal data servers 38 for storage in one of the databases associated with the storage device 40. It should be appreciated that such data may be communicated within the hospital 28, 30 via use of one or more wired or wireless networks. For example, certain of the devices associated with the hospital 28, 30 such as the PC's 48 may be coupled to the data server 38 via a wired network (e.g., ethernet), whereas other components such as the patient-care devices 44 may support wireless communication to the data server 38. Moreover, other types of devices may also be utilized to input patient data (e.g., a personal digital assistant (PDA) or a bar code scanner for scanning a patient bracelet or the like) and would likewise communicate to the data server 38 via either a wired or wireless connection.

The communications servers 42 of the hospital networks 24, 26 communicate patient data maintained within the hospital databases to the repository network 12 via the internet 32. The communications servers 42 may be configured to communicate to the repository network 12 by use of any of numerous communications protocols. For example, the communications server 42 may be configured as an electronic mail (e-mail) server which "packages" updated patient data into e-mail messages which are then mailed to the repository network 12 via the internet 32. Alternatively, the communications server 42 may be configured as a file transfer protocol (FTP) or hyper text transfer protocol (HTTP) server which is configured to transfer files containing patient data to the repository network 12. It should be appreciated that any other communications protocol may also be utilized including secure communications protocols for ensuring the security of the transmitted information.

The repository network 12, in turn, utilizes a corresponding server configuration to receive the transferred data from the communications servers 42. In particular, the hospital-interface server 14 of the repository network 12 may be configured in a similar manner as the communications servers 42 of the various hospitals in order to communicate therewith. For example, when the hospital's communications servers 42 are configured as e-mail servers, the hospital-interface server 14 of the repository network 12 may also be configured as an e-mail server thereby allowing for transfer of e-mail messages between the two servers. Similarly, the hospital-interface server 14 may also be configured as an FTP and/or HTTP server if any or all of the hospital data servers 42 are so configured. It should be appreciated that the hospital-interface server 14 of the repository network 12 may be configured to communicate with the hospital communications servers 42 in any number of different protocols in order to provide for flexibility in the manner in which data is received by the repository network 12.

The internal data server 16 associated with the repository network 12 stores or otherwise processes the received information from the hospital networks 24, 26 into the appropriate fields of the patient databases 22 maintained in the storage devices 20. For example, the internal data server 16 may be configured to periodically parse any incoming e-mail messages from the hospital networks 24, 26 into the appropriate data fields and then store the same in one of the patient databases 22. In the case of use of an FTP or HTTP transfer protocol, the data server 16 extracts relevant data from a transferred file and likewise stores the same in one of the patient databases 22.

The subscriber-interface server 18 is provided to interface with the subscribers 34, 36. As such, the subscriber-interface server 18 performs such tasks as authenticating subscribers in order to allow access to the database, administers subscriber accounts (adds new accounts, deletes accounts, and/or changes subscription levels), formats subscriber queries (i.e., data requests), accesses the patient database 22 to fulfill subscriber queries (or interfaces with the internal data server 16 to access the database 22), formats the retrieved data for the subscriber, and transmits the requested data to the subscribers 34, 36. In one exemplary embodiment, the subscriber-interface server 18 is configured as a web server which allows for interaction between the repository network 12 and the subscribers 34, 36 via the internet 32.

Hence, as described herein, the data system 10 may be operated to provide realtime or near-realtime patient data to the subscribers 34, 36. In particular, data collected by the hospital networks 24, 26 is initially stored in the hospital storage devices 40. Specifically, during operation of the patient-care devices 44, device data generated by the patient-care devices 44 are transmitted via the hospital network 24, 26 to the storage devices 40 for entry into the databases associated therewith. Similarly, sensory data generated by the sensors 46 is likewise transmitted via the hospital network 24, 26 to the storage devices 40 for entry into the databases associated therewith. Moreover, any data entered via the PC's or PDA's 48 (e.g., diagnostic codes and/or treatment codes) is likewise transmitted via the hospital network 24, 26 to the storage devices 40 for entry into the databases associated therewith. If the patient is a new patient, initial patient information such as patient identification code and/or demographic information may be transmitted from the PC 48 which is utilized to enter such manual patient data to the databases associated with the storage devices 40.

Figure 2:
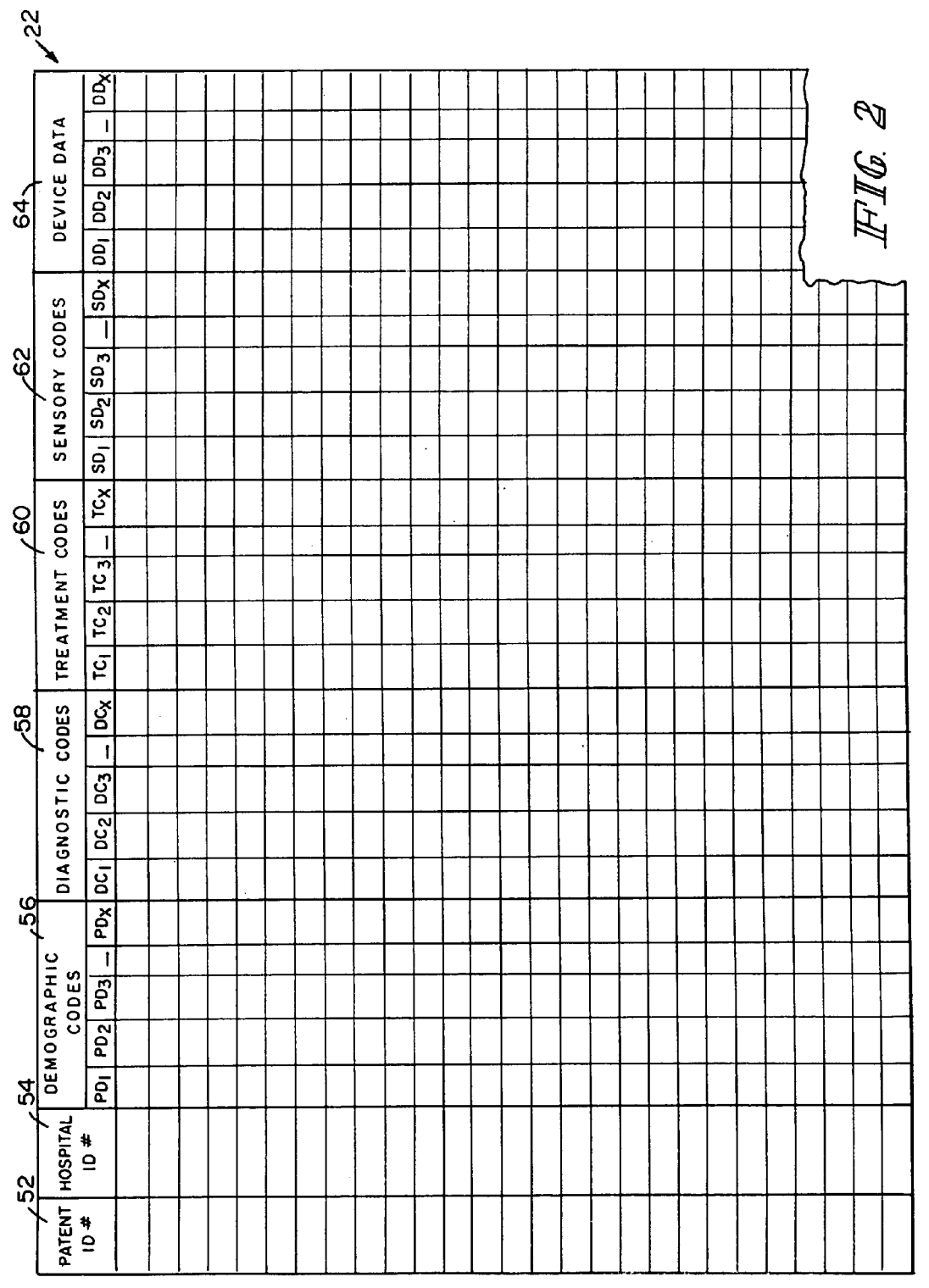

Either upon receipt of any newly received data, or at regularly scheduled short intervals, the hospital communications server 42 queries the hospital database 40 in order to retrieve the newly received data. The communications server 42 then "packages" the data into formatted files (e.g., e-mail messages or FTP/HTTP files) and thereafter transmits the data to the repository network 12 via the internet 32. The hospital-interface server 14 of the repository network 12 receives such a data transmission from the hospital network 24, 26 and presents the received files to the data server 16 which parses or otherwise processes the data in the transmitted file into a format suitable for storage in the patient database 22. For example, an exemplary data structure for maintenance of the patient database 22 is shown in FIG. 2. Amongst other things, the patient database 22 is configured to include a field 52 which includes a unique patient identification number assigned to each patient, along with a field 54 which includes a hospital identification number associated with the hospital or care facility at which patient is located. The patient database 22 also includes a field or plurality of fields 56 in which personal data ($PD_1$–$PD_x$) such as age, weight (i.e., initial, non-sensed weight), height, race, sex, or other information associated with the patient are maintained. The patient database 22 further includes a field or plurality of fields 58 in which the diagnostic codes ($DC_1$–$DC_x$) associated with the patient's ailment or condition are maintained. Similarly, the patient database 22 also includes a field or plurality of fields 60 in which the treatment codes ($TC_1$–$TC_x$) associated with the procedures and/or medications which are being utilized to treat the patient's ailment or condition are maintained.

Yet further, the patient database 22 is configured to include a number of data fields 62 for maintaining the sensory data ($SD_1$–$SD_x$) generated by the sensors 46 which are monitoring the patient. For example, both historical and current data associated with the patient's skin temperature, saturated oxygen level, respiratory rate, blood pressure, heart rate, or other forms of sensed data are maintained in the data fields 62. In a similar manner, the patient database 22 is also configured to include a number of data fields 64 for maintaining the device data ($DD_1$–$DD_x$) generated by the point of care devices 44 which are utilized in the treatment of the patient. For example, both current and historical data indicative of the air temperature, the rate at which any intravenous medications are being administered, the oxygen and/or moisture content of the air within the device, the rate at which air is circulated within the device, the time period in which the device is open to the ambient atmosphere, or other forms of device data are stored in the data fields 64.

It should be appreciated that the configuration of the patient database 22 described herein and shown in FIG. 2 is exemplary in nature. As such, the configuration of the patient database 22 may be altered to fit the needs of a given design of a data system 10. Moreover, it should also be appreciated that multiple databases 22, some of which may have redundant information, may also be maintained in order to fit the needs of a given data system 10 or tailored for a particular medical specialty.

As described above, data within the patient database 22 may be accessed by the subscribers 34, 36. The subscribers 34, 36 may take many forms including research groups, insurance organizations, the hospitals themselves (i.e., a given hospital may be both a data provider and a subscriber), individual doctors, pharmaceutical or medical device companies, or any other entity that may have an interest in the data being collected by the repository network 12. Typically, the subscribers 34, 36 would access the patient database 22 with a personal computer by use of a web browser. In particular, the subscriber's PC connects via the internet 32 to the subscriber-interface server 18 and thereafter transmits a data request to the server 18. The subscriber-interface server 18 validates or otherwise determines if the particular subscriber is entitled to access the patient database 22, and if so, to what subscription "level". Specifically, in one exemplary embodiment, subscribers may subscribe at various subscription levels based on the subscribers's data needs. In essence, the greater the subscribers data needs, the greater the cost associated with the subscription. Subscription levels and the costs associated therewith may also be varied based on, for example, connection time to the repository network 12, quantity and/or classification of data needed by the subscriber, timeliness of data needed (e.g., realtime/near-realtime versus archived data), and/or connection type to the repository network 12 (e.g., direction connection versus web-based access).

In any event, once the subscriber-interface server 18 has validated the subscriber's identification and subscription level, the server 18 begins to process the subscriber's data request. In doing so, the subscriber-interface 18 itself may query the patient database 22 or may, in the alternative, communicate the data request to the internal data server 16 which would then query the patient database 22. In either case, the requested data is retrieved from the patient database 22, formatted into a desired format, and then transmitted to the subscriber 34, 36 via the internet 32 by the subscriber-interface server 18.

Figure 3:
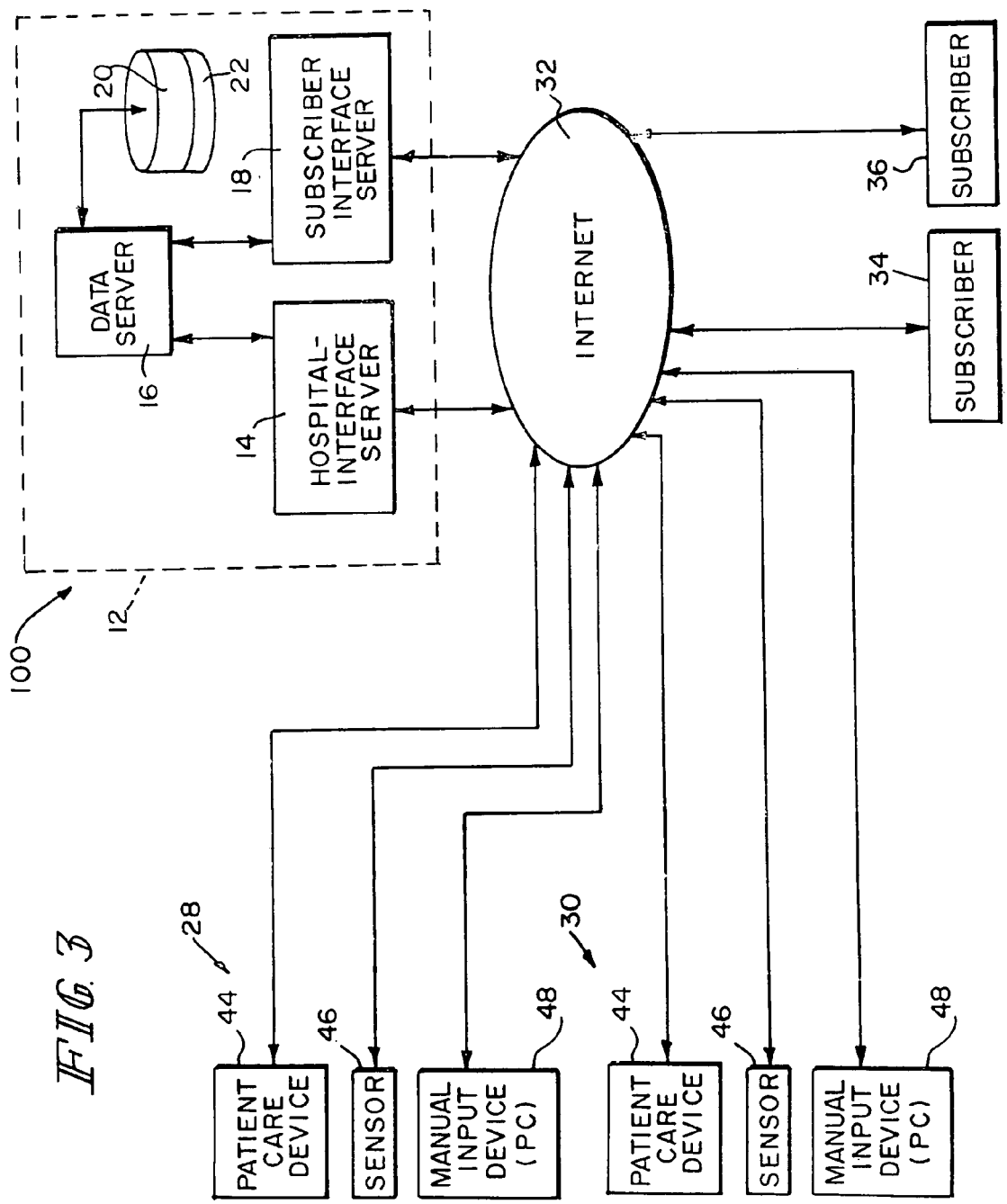
FIG. 3 is a block diagram, similar to FIG. 1, of another embodiment of a patient point-of-care data collection and distribution system according to this disclosure showing a repository network coupled to the Internet, a plurality of patient point-of-care data collection devices coupled to the Internet, and a plurality of subscribers coupled to the Internet.

Referring now to FIG. 3, there is shown another exemplary embodiment of a patient point-of-care data system (hereinafter designated with reference numeral 100) in accordance with this disclosure. The data system 100 is somewhat similar to the data system 10. As such, the same reference numerals have been utilized in FIG. 3 to designate similar components to those components previously discussed in regard to FIGS. 1 and 2, and additional discussion thereof is not warranted. The primary difference between the data system 10 and the data system 100 is that the data system 100 does not utilize a central server/database arrangement at each of the individual hospitals 28, 30, but rather utilizes devices which are configured to communicate directly with the repository network 12 via the internet 32.

In particular, as shown in FIG. 3, the patient-care devices 44 may be configured with networking hardware such as a modem or data router to provide for direct connection to the internet 32 thereby allowing the patient-care devices 44 to communicate directly with the repository network 12 via the internet 32. Similarly, the control hardware to which the sensors 46 are coupled may likewise be configured with networking hardware such as a modem or data router to provide for direct connection to the internet 32 thereby allowing the control hardware associated with the sensors 46 to communicate directly with the repository network 12 via the internet 32. Yet further, the PC's 48 may also be equipped with networking hardware such as a modem or data router to allow manual data input therewith to be communicated directly to the repository network 12 via the internet 32.

The configuration of the data system 100 is particularly useful in the case of when a given hospital may, for example, not have an existing network infrastructure. In particular, if a given hospital does not have an existing network infrastructure, the concepts disclosed herein may be utilized without requiring significant capital expenditures on the part of the hospital in order to design, construct, and implement such a network. It should also be appreciated that the repository network 12 may be configured (e.g., by use of multiple types of hospital-interface servers) to receive data from both types of hospitals (i.e., hospitals with and without a centralized network structure).

Figure 4:
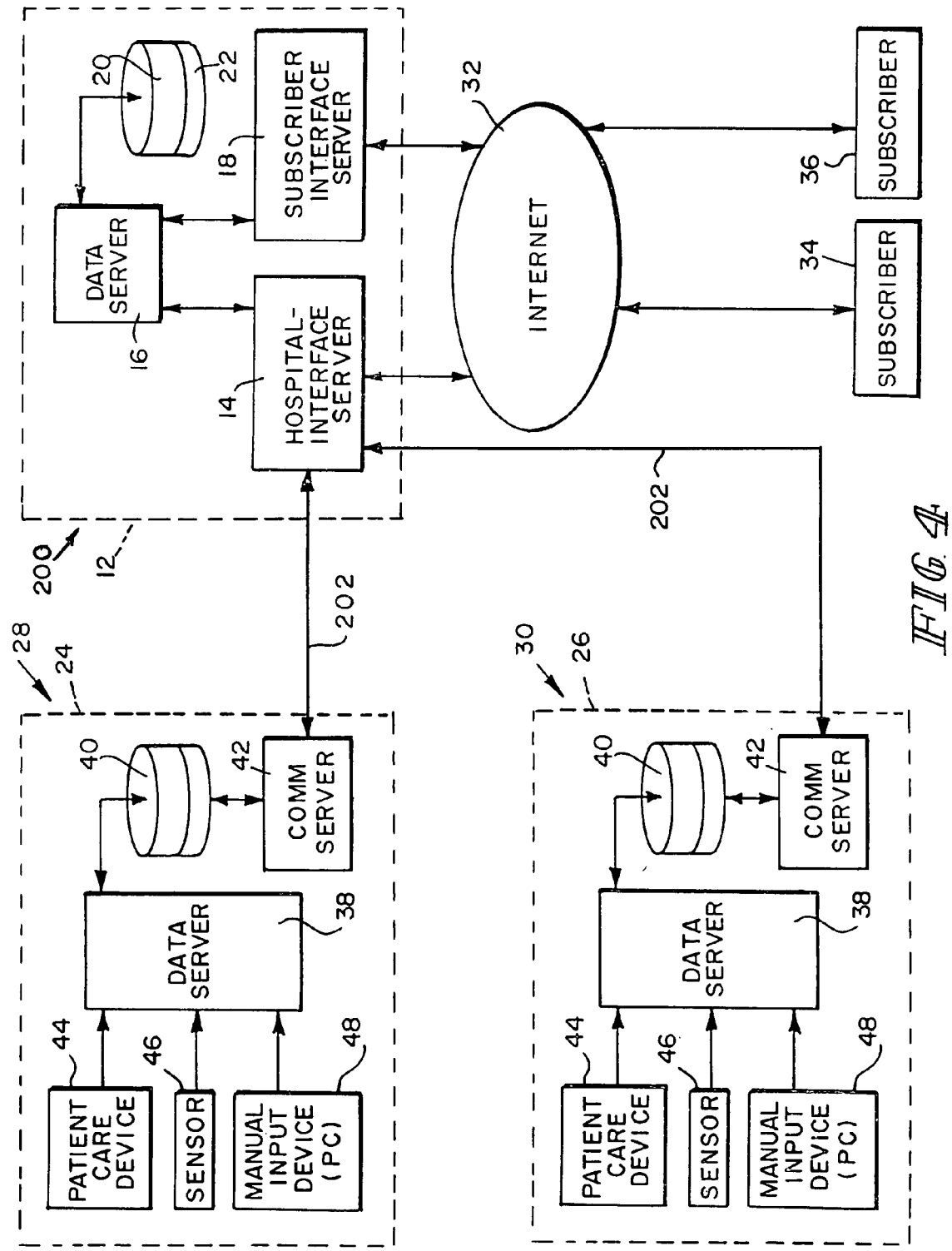
FIG. 4 is a block diagram, similar to FIG. 1, of yet another embodiment of a patient point-of-care data collection and distribution system according to this disclosure showing a repository network having a hospital-interface server and a subscriber-interface server, a plurality of hospital computer systems coupled to the hospital-interface server of the repository network via direct connections, the subscriber-interface server of the repository network coupled to the Internet, and a plurality of subscribers coupled to the Internet.

Referring now to FIG. 4, there is shown yet another exemplary embodiment of a patient point-of-care data system (hereinafter designated with reference numeral 200) in accordance with this disclosure. The data system 200 is somewhat similar to the data systems 10, 100. As such, the same reference numerals have been utilized in FIG. 4 to designate similar components to those components previously discussed in regard to FIGS. 1–3, and additional discussion thereof is not warranted. The primary difference between the data system 200 and the data systems 10, 100 is that the data system 200 does not utilize the internet 32 to communicate with the data repository, but rather communicates directly with the repository network 12 via a direct connection 202.

For example, the direct connection 202 may be in the form of a telephony connection utilizing a point-to-point protocol (PPP) to connect and thereafter communicate with the repository network 12. Such a configuration may be utilized if it were desirable to avoid use of a publicly-accessible global network such as the internet 32. It should also be appreciated that the repository network 12 may be configured (e.g., by use of multiple types of hospital-interface servers) to receive data from hospitals configured in any of the above described manners. In particular, the repository network 12 may be configured to include interface servers for receiving data transmissions both via the internet 32 (as described above in regard to the data systems 10 and 100) and via the direct connection 202.

It should be appreciated that other configurations of patient point-of-care data systems are also contemplated for use according to this disclosure. For example, in lieu of actually storing patient data in the storage devices associated with the repository network 12 (i.e., the storage devices 20), the patient data may actually be maintained at each of the individual hospital networks. In such a configuration, the databases associated with the repository network 12 would be utilized to maintain an index of the patient data stored at each of the external locations (i.e., each of the hospitals). As such, when a subscriber 34, 36 requests particular information, the servers associated with the repository network 12 determine the location of, and thereafter retrieve, relevant data from the numerous hospital networks. The retrieved data may then be formatted for presentation to the subscriber 34, 36. It should also be appreciated that in lieu of actually retrieving the data for the subscriber 34, 36, the repository network 12 may be configured to simply provide the subscriber with the network address of the patient data stored on the hospital networks, along with authentication information for accessing the same, in order to allow the subscriber to access the hospital network directly.

Hence, as described herein, the patient point-of-care data systems of the present disclosure have numerous advantages over heretofore designed healthcare data systems. For example, the data systems of the present disclosure allow for the collection and distribution of realtime or near-realtime patient data relating to the treatment of a large number of different patients being cared for at a large number of different hospitals. Specifically, unlike heretofore designed internal hospital networks such as hospital LAN's or the like, the data systems of the present disclosure provide for the collection and distribution of patient data relating to patients which are located in a relatively large number of different hospitals. In this manner, research may be quickly and easily performed across a large geographical area. Such a system also provides for a relatively large sample size of patients since data associated with a large number of patients may be utilized.

Moreover, by collecting sensory data and device data, in addition to diagnostic data and treatment data, the patient's condition may be monitored on a substantially realtime or near-realtime basis (based on the interval in which data is transmitted to the repository network 12 from the hospitals). Such sensory data and device data is particularly useful in regard to tracking a patient's response to certain treatments and medications.

Yet further, the data systems in accordance with this disclosure allow for the dissemination of patient data to a large number of subscribers that may otherwise be forced to expend a large number of resources to collect such data. For example, a pharmaceutical company may access the patient database 22 in order to track the response to patients which have been administered a drug which is manufactured by the company. Similarly, the pharmaceutical company may also utilize the patient database 22 for marketing purposes. For example, the company may utilize the patient database 22 to determine the percentage of patients which are afflicted with a particular ailment that are being treated with the company's drug or drugs.

According to this disclosure, therefore, a method of patient data management comprises any one or more of the following steps, in any combination:

collecting patient point-of-care data on a substantially realtime basis;

distributing patient point-of-care on a substantially realtime basis;

identifying a plurality of hospitals, each of which has a unique hospital code;

identifying a plurality of patients with the plurality of hospitals, each of which has a unique patient code;

identifying patient point-of-care data associated with each of the plurality of patients;

identifying demographic data associated with each of the plurality of patients;

identifying diagnostic data associated with each of the plurality of patients;

identifying treatment data associated with each of the plurality of patients;

identifying sensory data generated by a number of sensors which are utilized to sense a number of conditions associated with each of the plurality of patients;

identifying device data generated by a number of patient-care devices which are utilized in the treatment of each of the plurality of patients;

transmitting the unique hospital codes to a repository network;

transmitting the unique patient code to the repository network;

transmitting patient data associated with each of the plurality of patients to the repository network;

transmitting demographic data associated with each of the plurality of patients to the repository network;

transmitting diagnostic data associated with each of the plurality of patients to the repository network;

transmitting treatment data associated with each of the plurality of patients to the repository network;

transmitting sensory data generated by a number of sensors which are utilized to sense a number of conditions associated with each of the plurality of patients to the repository network;

transmitting device data generated by a number of patient-care devices which are utilized in the treatment of each of the plurality of patients to the repository network;

transmitting the unique hospital codes to a repository network via a global network;

transmitting the unique patient code to the repository network via a global network;

transmitting patient point-of-care data associated with each of the plurality of patients to the repository network via a global network;

transmitting demographic data associated with each of the plurality of patients to the repository network via a global network;

transmitting diagnostic data associated with each of the plurality of patients to the repository network via a global network;

transmitting treatment data associated with each of the plurality of patients to the repository network via a global network;

transmitting sensory data generated by a number of sensors which are utilized to sense a number of conditions associated with each of the plurality of patients to the repository network via a global network;

transmitting device data generated by a number of patient-care devices which are utilized in the treatment of each of the plurality of patients to the repository network via a global network;

storing the unique hospital codes in a patient database associated with the repository network;

storing the unique patient code in a patient database associated with the repository network;

storing patient data associated with each of the plurality of patients in a patient database associated with the repository network;

storing demographic data associated with each of the plurality of patients in a patient database associated with the repository network;

storing diagnostic data associated with each of the plurality of patients in a patient database associated with the repository network;

storing treatment data associated with each of the plurality of patients in a patient database associated with the repository network;

storing sensory data generated by a number of sensors which are utilized to sense a number of conditions associated with each of the plurality of patients in a patient database associated with the repository network;

storing device data generated by a number of patient-care devices which are utilized in the treatment of each of the plurality of patients in a patient database associated with the repository network;

retrieving the unique patient code from the patient database associated with the repository network;

retrieving patient data associated with each of the plurality of patients from the patient database associated with the repository network;

retrieving demographic data associated with each of the plurality of patients from the patient database associated with the repository network;

retrieving diagnostic data associated with each of the plurality of patients from the patient database associated with the repository network;

retrieving treatment data associated with each of the plurality of patients from the patient database associated with the repository network;

retrieving sensory data generated by a number of sensors which are utilized to sense a number of conditions associated with each of the plurality of patients from the patient database associated with the repository network;

retrieving device data generated by a number of patient-care devices which are utilized in the treatment of each of the plurality of patients from the patient database associated with the repository network;

transmitting the unique patient code retrieved from the patient database associated with the repository network to a subscriber;

transmitting patient data associated with each of the plurality of patients that was retrieved from the patient database associated with the repository network to a subscriber;

transmitting demographic data associated with each of the plurality of patients that was retrieved from the patient database associated with the repository network to a subscriber;

transmitting diagnostic data associated with each of the plurality of patients that was retrieved from the patient database associated with the repository network to a subscriber;

transmitting treatment data associated with each of the plurality of patients that was retrieved from the patient database associated with the repository network to a subscriber;

transmitting sensory data generated by a number of sensors which are utilized to sense a number of conditions associated with each of the plurality of patients that was retrieved from the patient database associated with the repository network to a subscriber;

transmitting device data generated by a number of patient-care devices which are utilized in the treatment of each of the plurality of patients that was retrieved from the patient database associated with the repository network to a subscriber;

formatting data retrieved from the patient database prior to transmission thereof to a subscriber;

varying the content of data retrieved and transmitted to a subscriber based on the subscribers subscription level.

Further according to this disclosure, a data system comprises:

a storage device for maintaining a patient database;

a processing unit electrically coupled to the storage device; and a memory device electrically coupled to the processing unit, wherein the memory device has stored therein a plurality of operating instructions which, when executed by the processing unit, causes the processing unit to do one or more of the following, or any combination thereof:

identify a plurality of hospitals, each of which has a unique hospital code;

identify a plurality of patients with the plurality of hospitals, each of which has a unique patient code;

identify patient data associated with each of the plurality of patients;

identify demographic data associated with each of the plurality of patients;

identify diagnostic data associated with each of the plurality of patients;

identify treatment data associated with each of the plurality of patients;

identify sensory data generated by a number of sensors which are utilized to sense a number of conditions associated with each of the plurality of patients;

identify device data generated by a number of patient-care devices which are utilized in the treatment of each of the plurality of patients;

transmit the unique hospital codes to a repository network;

transmit the unique patient code to the repository network;

transmit patient data associated with each of the plurality of patients to the repository network;

transmit demographic data associated with each of the plurality of patients to the repository network;

transmit diagnostic data associated with each of the plurality of patients to the repository network;

transmit treatment data associated with each of the plurality of patients to the repository network;

transmit sensory data generated by a number of sensors which are utilized to sense a number of conditions associated with each of the plurality of patients to the repository network;

transmit device data generated by a number of patient-care devices which are utilized in the treatment of each of the plurality of patients to the repository network;

transmit the unique hospital codes to a repository network via a global network;

transmit the unique patient code to the repository network via a global network;

transmit patient data associated with each of the plurality of patients to the repository network via a global network;

transmit demographic data associated with each of the plurality of patients to the repository network via a global network;

transmit diagnostic data associated with each of the plurality of patients to the repository network via a global network;

transmit treatment data associated with each of the plurality of patients to the repository network via a global network;

transmit sensory data generated by a number of sensors which are utilized to sense a number of conditions associated with each of the plurality of patients to the repository network via a global network;

transmit device data generated by a number of patient-care devices which are utilized in the treatment of each of the plurality of patients to the repository network via a global network;

store the unique hospital codes in a patient database associated with the repository network;

store the unique patient code in a patient database associated with the repository network;

store patient data associated with each of the plurality of patients in a patient database associated with the repository network;

store demographic data associated with each of the plurality of patients in a patient database associated with the repository network;

store diagnostic data associated with each of the plurality of patients in a patient database associated with the repository network;

store treatment data associated with each of the plurality of patients in a patient database associated with the repository network;

store sensory data generated by a number of sensors which are utilized to sense a number of conditions associated with each of the plurality of patients in a patient database associated with the repository network;

store device data generated by a number of patient-care devices which are utilized in the treatment of each of the plurality of patients in a patient database associated with the repository network;

retrieve the unique patient code from the patient database associated with the repository network;

retrieve patient data associated with each of the plurality of patients from the patient database associated with the repository network;

retrieve demographic data associated with each of the plurality of patients from the patient database associated with the repository network;

retrieve diagnostic data associated with each of the plurality of patients from the patient database associated with the repository network;

retrieve treatment data associated with each of the plurality of patients from the patient database associated with the repository network;

retrieve sensory data generated by a number of sensors which are utilized to sense a number of conditions associated with each of the plurality of patients from the patient database associated with the repository network;

retrieve device data generated by a number of patient-care devices which are utilized in the treatment of each of the plurality of patients from the patient database associated with the repository network;

transmit the unique patient code retrieved from the patient database associated with the repository network to a subscriber;

transmit patient data associated with each of the plurality of patients that was retrieved from the patient database associated with the repository network to a subscriber;

transmit demographic data associated with each of the plurality of patients that was retrieved from the patient database associated with the repository network to a subscriber;

transmit diagnostic data associated with each of the plurality of patients that was retrieved from the patient database associated with the repository network to a subscriber;

transmit treatment data associated with each of the plurality of patients that was retrieved from the patient database associated with the repository network to a subscriber;

transmit sensory data generated by a number of sensors which are utilized to sense a number of conditions associated with each of the plurality of patients that was retrieved from the patient database associated with the repository network to a subscriber;

transmit device data generated by a number of patient-care devices which are utilized in the treatment of each of the plurality of patients that was retrieved from the patient database associated with the repository network to a subscriber;

format data retrieved from the patient database prior to transmission thereof to a subscriber;

vary the content of data retrieved and transmitted to a subscriber based on the subscribers subscription level.

Figure 5:
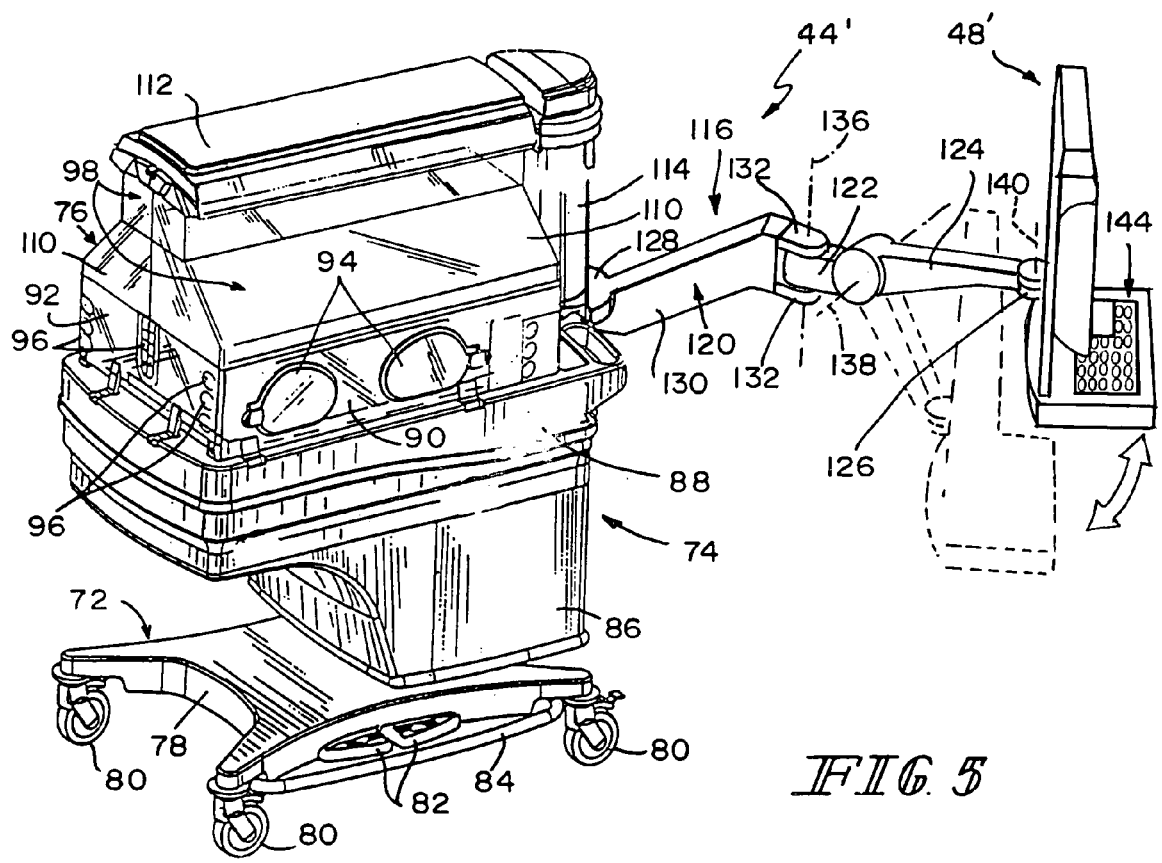
FIG. 5 is a perspective view of a patient care device configured for collecting patient point-of-care data in accordance with this disclosure, showing the patient support device having an wheeled base, an infant support platform above the base, an infant enclosure above the infant support platform, an arm assembly extending from the infant support platform, and a computer coupled to the arm assembly.

Referring now to FIGS. 5—5, an illustrative patient care device 44' comprises a base 72, an infant support platform 74 above base 72, and an infant compartment 76 above platform 74 as shown in FIG. 5. The illustrative patient care device 44' is an infant thermal support device that is operable as an infant incubator, an infant radiant warmer, or both. However, the features of device 44' described below with reference to FIGS. 5–25 are applicable to other types of patient care devices, such as hospital beds, infant incubators, infant radiant warmers, stretchers, surgical tables or any other type of device on which patients rest in a healthcare environment, including chairs, wheelchairs, and devices having mattresses or therapeutic surfaces, including rotation mattresses, percussion mattresses, low airloss mattresses, or fluidized bead surfaces. The term "mattress" and "mattresses" as used in this disclosure, including in the claims, is intended to cover all types of person-support elements including single-layer mattresses, multi-layer mattresses, zoned mattresses, foam mattresses, inflatable air bladders, and any of the therapeutic surfaces listed in the preceding sentence, as well as combinations and equivalents of these and as well as any other type of cushion known for supporting a person.

Illustrative base 72 has a structure or frame 78, a set of casters or wheels 80 coupled to frame 78, a set of foot pedals 82 that are engaged by a caregiver to operate a drive mechanism (not shown) to change the elevation of platform 74 relative to base 72, and a set of bumpers 84 that protect pedals 82 from inadvertent impacts. Platform 74 includes a lower portion 86 that shields the drive mechanism and other components of device 44 from view. Platform 74 also includes an upper portion 88 that carries components of a humidification system (not shown) of device 44 and that carries components of a convective heating system (not shown).

Infant compartment 76 includes a pair of sidewalls 90 and a pair of end walls 92. A pair of access doors 94 are coupled to each sidewall 90 and are movable between respective closed positions, shown in FIG. 5, covering respective access ports (not shown) formed in the sidewalls 90 and opened positions (not shown) uncovering the respective access ports to allow a caregiver to gain access to an infant in a patient space defined by the infant compartment 76. End walls 92 each include one or more line passthroughs through which electrical lines and fluid lines are routed into the patient space. Some or all of sidewalls 90 and end walls 92 are pivotable from respective raised positions, shown in FIG. 5, to lowered positions (not shown) to provide caregivers with an increased amount of access to the infant situated in infant compartment 76.

Infant compartment 76 further includes a canopy 98 having a pair of canopy halves 110 as shown in FIG. 5. Device 44' includes an overhead arm 112 to which canopy halves 110 are coupled for pivoting movement between lowered positions, shown in FIG. 5, in which lower edges of the canopy halves are in close proximity to upper edges of sidewalls 90 and end walls 92 to substantially enclose the patient space and raised positions (not shown) to provide increased access to the infant in the patient space. One or more sources of infrared radiation (not shown) are mounted to an underside of arm 112 and, when activated, provide radiant heat to the patient space to warm the infant. Device 44' includes a column 114 having an upper end from which overhead arm 112 extends in a cantilevered manner. Column 114 is telescopically extendable and retractable to vertically raise and lower, respectively, canopy 98, arm 112, and the source(s) of infrared radiation as a unit. Device 44' has a drive mechanism that is operable to extend and retract column 114.

Device 44' also includes a computer support 116 and a computer 48' coupled to support 116 as shown in FIGS. 5–8. Computer 48' is configured to receive patient point-of-care data from the patient supported on device 44' and from device 44' itself. Computer 48' has a display screen 118 on which the patient point-of-care data is displayed in various combinations depending upon commands received by computer 48' from a user as described below in further detail. In addition, computer 48' is configured to transmit data, including patient point-of-care data associated with device 44' and the patient supported thereon, to the hospital network and to retrieve from the network various types of data, including patient point-of-care data associated with other devices substantially similar to device 44' and the patients supported thereon, from the network. Thus, patient point-of-care data associated with device 44' and the patient supported thereon, as well as other types of data retrievable by computer 48' from the network, is viewable on screen 118 of computer 48' at the point of care. The types of data displayed on screen 118 is described in detail below with reference to FIGS. 9–25. However, it is within the scope of this disclosure for other types of data, including any of the data described above with reference to FIGS. 1–4, to be displayed on screen 118 in addition to or in lieu of the data described below.

Figure 7:
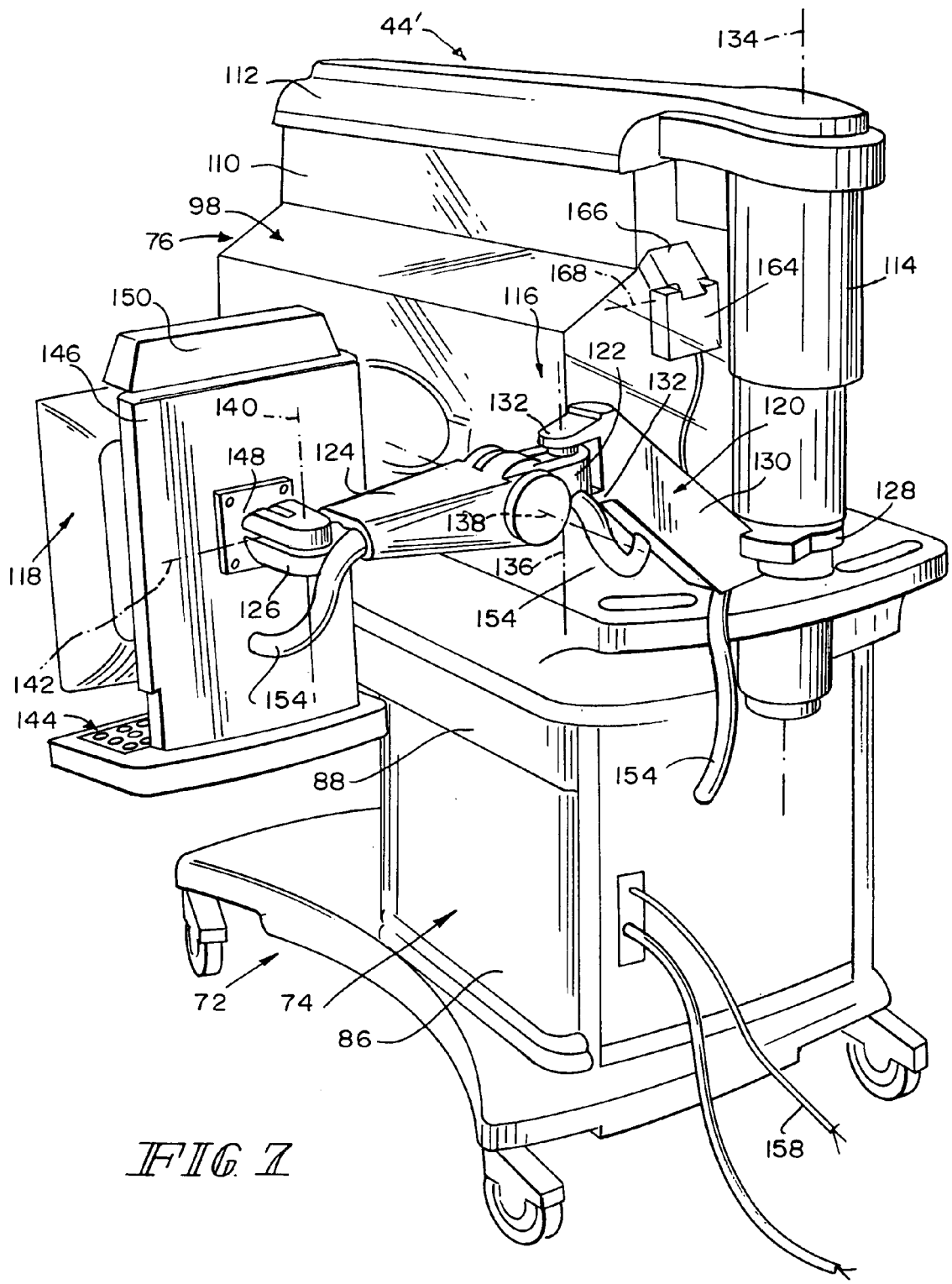
FIG. 7 is a rear perspective view of the patient care device of FIG. 5 showing a number of axes (in phantom) about which arms of the arm assembly are pivotable relative to the infant support platform and about which the computer is pivotable relative to the arm assembly.

Illustrative computer support 116 is an arm assembly (hereinafter referred to as "arm assembly 116") that is configured to permit computer 48' to be repositioned relative to the remainder of device 44'. Arm assembly 116 has a first arm 120, a first clevis 122, a second arm 124, and a second clevis 126 as shown in FIGS. 5 and 7. First arm 120 has a collar portion 128 coupled to a lower region of column 114, a main portion 130 angling outwardly and upwardly from collar portion 128, and a pair of flanges 132 extending substantially horizontally outwardly from portion 130. Arm 120 is pivotable about a first vertical axis 134 which is defined by the interconnection between column 114 and collar portion 128. First clevis 126 is coupled to flanges 132 for pivotable movement about a second vertical axis 136 and second arm 124 is coupled to first clevis 126 for pivotable movement about a first horizontal axis 138. Second clevis 126 is coupled to an outer end of second arm 124 for pivotable movement about a third vertical axis 140 and computer 48' is coupled to second clevis 126 for pivotable movement about a second horizontal axis 142.

Second arm 124 is a counterbalance arm having counterbalance elements, such as springs or dashpots, that provide a counterbalance force sufficient to counterbalance the weight of computer 48' so that computer 48' remains in place after computer 48' and arm 124 have been adjusted about axis 138 to a desired position. In addition, second arm 124 includes an orientation mechanism, such as a parallelogram linkage, that maintains the orientation of clevis 126 and computer 48' relative to the ground as arm 124 pivots about axis 138. For example, if display screen 118 is substantially vertical in orientation and faces away from arm 120 when arm 124 is in a lowered position, as shown in FIG. 5 (in phantom), and then arm 124 is pivoted about axis 138 to any other position, such as an intermediate position shown in FIG. 5 (in solid), the orientation mechanism maintains display screen 118 in the substantially vertical orientation facing away from arm 120 as arm 124 moves between the lowered position and the intermediate position. Additional details of counterbalance arms are shown and described in U.S. Pat. Nos. 6,012,693; 5,992,809; 5,842,672; 5,826,846; 5,743,503 and 5,340,072, each of which is hereby incorporated by reference herein.

In the illustrative embodiment, pivoting movement of arm 120 about vertical axis 134 is the only degree of freedom of arm 120 relative to column 114. As a result, the height of flanges 132 and clevis 122 above the floor on which device 44' sets remains substantially the same as arm 120 pivots about axis 138. Of course, adjusting the height of platform 74 relative to base 72 will also adjust the height of arm 120 relative to the floor. Pivoting movement of clevis 122 about vertical axis 136 is the only degree of freedom of clevis 122 relative to arm 120 and pivoting movement of arm 124 about horizontal axis 138 is the only degree of freedom of arm 124 relative to clevis 122. In addition, pivoting movement of clevis 126 about vertical axis 140 is the only degree of freedom of clevis 126 relative to arm 124 and pivoting movement of computer 48' about horizontal axis 142 is the only degree of freedom of computer 48' relative to clevis 126. However, it is within the scope of this disclosure for computer support 116 to have a different number of linkage elements and for the interconnection between adjacent linkage elements to have multiple degrees of freedom (e.g. pivoting about multiple axes, telescopic movement, or linear extension/retraction).

In some embodiments of arm assembly 116, one or more stops, such as lugs, pins, surfaces and the like, are included in or provided at the interface between elements 114, 120, 122, 124, 126, 48' to limit the amount of movement of these elements about the respective pivot axes 134, 136, 138, 140, 142. In addition, some embodiments of arm assembly 116 include various anti-friction components, such as thrust bearings, radial bearings, plain bearings, bushings and the like situated between elements 114, 120, 122, 124, 126, 48'. In one embodiment, friction couplings are provided at the interface between clevis 126 and computer 48' and between clevis 126 and arm 124. The friction couplings are configured such that typical forces imparted by a user to enter commands or data on a keyboard 144 or by touching display screen 118 do not cause computer 48' to move relative to arm 124. However, the friction couplings are configured such that application of a threshold amount of force to computer 48', which threshold force exceeds the typical forces associated with entering commands or data on keyboard 144 or screen 118, results in repositioning of computer 48' relative to arm 124.

Figure 6:
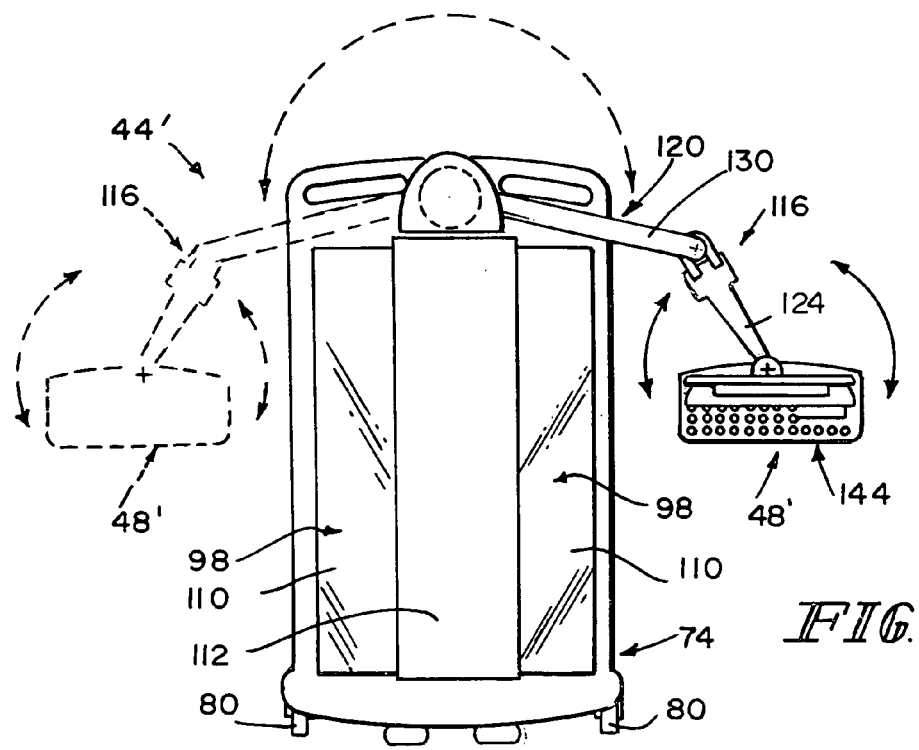
FIG. 6 is top plan view of the patient care device of FIG. 5 showing the arm assembly and computer being movable about a pivot axis between a first position (in solid) in which the computer is situated on a first side of the infant support platform and a second position (in phantom) in which the computer is situated on a second side of the infant support platform.

In the illustrative embodiment of device 44', arm assembly 116 and computer 48' are movable between a first position, shown in FIG. 6 (in solid), in which computer 48' is situated alongside a first side of platform 74 and infant compartment 76, and a second position, shown in FIG. 6 (in phantom), in which computer 48' is situated alongside a second side of platform 74 and infant compartment 76. Of course, arm assembly 116 and computer 48' are positionable in any of an infinite number of positions within the ranges of motion of elements 120, 122, 124, 126, 48'. Also in the illustrative embodiment, due to the fact that the length of arm 120 from axis 134 to axis 136 is longer than the lateral distance from axis 134 to the side of infant support platform 74, the majority of the positions in which computer 48' may be placed is outside the "footprint" of platform 74 and infant compartment 76. Thus, a user seated in a chair adjacent device 44' is able to place computer 48' in an appropriate position for use while sitting in the chair and a user standing alongside device 44' is able to place computer 44' in an appropriate position for use while standing.

The maneuverability of computer 48' into such a wide range of positions relative to the remainder of device 44' is an improvement over patient support devices that have computers integrated therein but that are either fixed in location on the device or that have limited mobility, such as only being movable within one or two degrees of freedom. In addition, by having computer 48' suspended away from the remainder of device 44' (i.e., outside the "footprint" of platform 74 and compartment 76), screen 118 and keyboard 144 are able to be made larger than if computer 48' and keyboard 144 were, for example, mounted on or supported directly by column 114, platform 74, or compartment 76.

Figure 8:
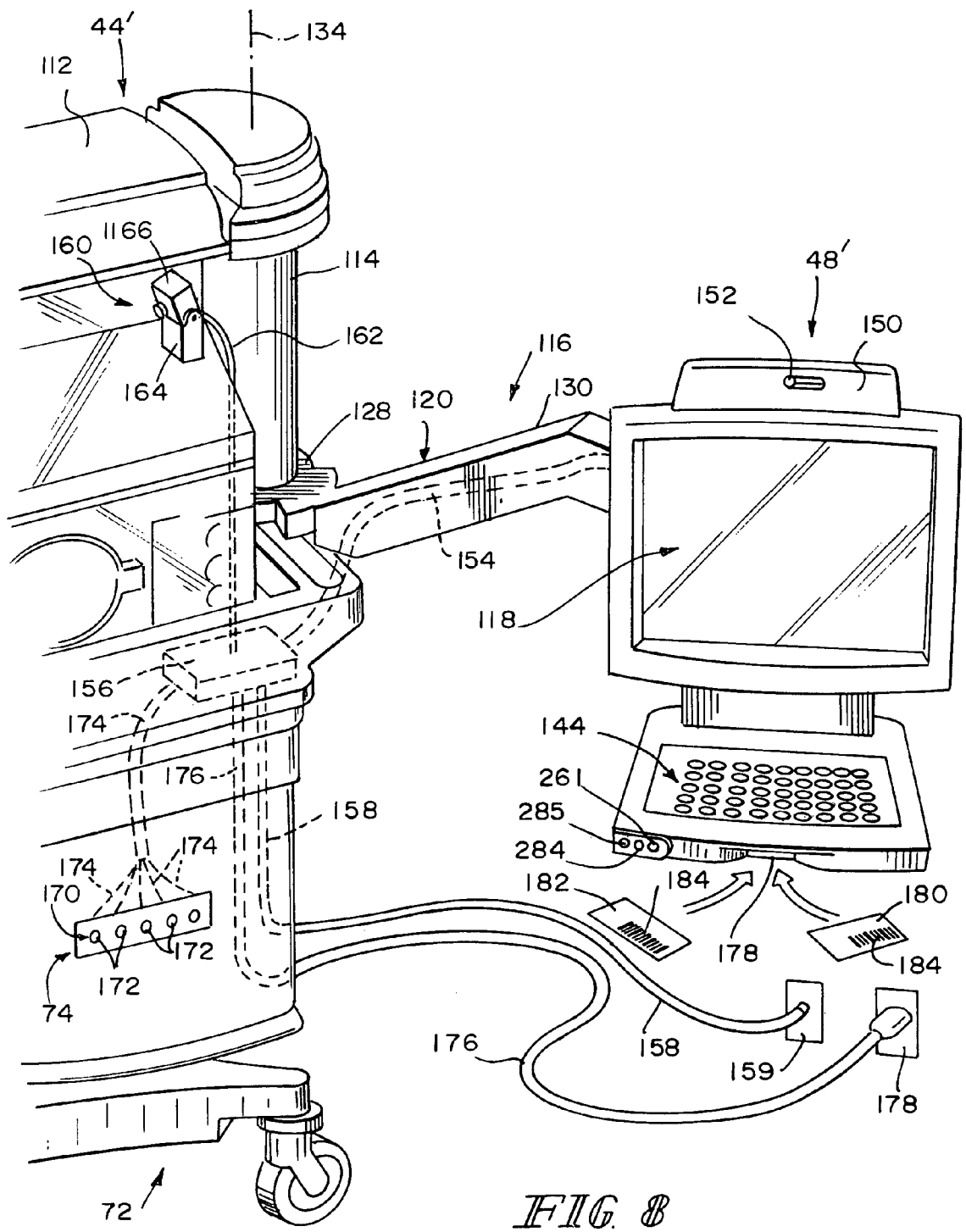
FIG. 8 is an enlarged perspective view of a portion of the patient care device of FIG. 5 showing a pair of tokens beneath the computer, the computer having a reader to which the tokens are presented, the computer being coupled via a first data line (in phantom) to a controller (in phantom) situated in an interior region of the infant support platform, a plurality of sensor connection ports accessible on a lower portion of the infant support platform beneath the controller, the connection ports being coupled to the controller via respective sensor data lines (in phantom), a camera coupled to the infant enclosure and coupled to the controller via a video data line (in phantom), and the controller being coupled to a data port of a hospital network via a second data line.

Illustrative computer 48' has a backing panel or plate 146 to which display screen 118 and keyboard 144 are coupled as shown best in FIG. 7. A bracket 148 is mounted to backing panel 146 and is coupled to clevis 126. A camera housing 150 is coupled to an upper portion of panel 146 and overhangs a portion of display screen 118. A video camera (not shown) is situated in an interior region of housing 150 and receives images through an aperture 152 formed in a front portion of housing 150 as shown in FIG. 8. Electrical wires associated with computer 48', such as power lines, data lines, video lines, and the like, are bundled into a cable 154 which is routed from panel 146 through interior regions of arm assembly 116 and into the interior region of platform 74 as shown in FIGS. 7 and 8. While most of cable 154 in the illustrative embodiment is situated in the interior regions of arm assembly 116, certain portions of cable 154 are situated outside of arm assembly 116 to accommodate articulation of arm assembly 116.

Device 44' includes a controller 156, shown diagrammatically in FIG. 8, that controls the operation of various functions of device 44'. Functions controlled by controller 156 include operation of the radiant heater, operation of the convective heating system, operation of the humidification system, raising/lowering of canopy 98, and raising/lowering of platform 74 relative to base 72. Controller 156 also receives various types of data from computer 48' and from a variety of other input devices. Furthermore, controller 156 transmits various types of data to computer 48' via the appropriate data lines in cable 154 and to the hospital network via a data line 158 which extends from controller 156 to a data port or wall outlet 159 of the healthcare facility. Data from the hospital network is communicated to controller 156 through line 158, as well. Thus, according to this disclosure, device 44' and computer 48' are not only capable of providing data, including patient point-of-care data, to any of systems 10, 100, 200, but are also capable of receiving data from systems 10, 100, 200. In other words, device 44' and computer 48' are configured to serve as subscribers 34, 36 of systems 10, 100, 200.

Device 44' includes one or more environmental sensors and other types of sensors, such as, for example, an air temperature sensor to sense the temperature in the patient space, a baby temperature sensor to sense temperature of the infant, a humidity sensor to sense the humidity in the patient space, a noise sensor to sense the noise levels to which the infant is exposed, light sensors to sense the light levels to which the infant is exposed, a fan speed sensor to sense the speed at which the fan of the convective heating system operates, a current sensor to sense the amount of current supplied to an associated one of the heaters of device 44', sensors that sense whether each of canopy halves 110 is in the respective raised or lowered position, and a sensor that senses the elevation of overhead arm 112. Appropriate electrical lines (not shown) are included in device 44' to interconnect the various sensors listed above, to controller 156. Moreover, controller 156 includes electrical circuitry that processes, conditions, converts, or otherwise manipulates the signals provided by the sensors included in device 44' into usable data. Thus, the signals provided by these various types of sensors provide some of the patient point-of-care data that is viewable on display screen 118 and that is transmitted to the hospital network and/or to the central database from which subscribers or authorized users are able to retrieve the data as described above.

Device 44' further includes a video camera 160 and a video data line 162 that extends from camera 160 to controller 156. Camera 160 includes a lower portion or mount 164 that is coupled to one of end walls 92 and an upper portion 166 that is pivotable about a transverse axis 168. Upper portion 166 of camera 160 is aimed at the infant supported in the patient space defined by infant compartment 74 and the video signal from camera 160, which contains image data of the infant, is communicated to controller 156 via line 162. Device 44' also has a connection port 170 which includes a plurality of connectors 172 to which external data lines or patient care modules (not shown) connect. A set of internal data lines 174 extend from each of connectors 172 to controller 156.

Some of the external data lines or patient care modules that connect to connectors 172 provide sensor data relating to various physiological conditions of the infant, such as heart rate, respiration rate, blood chemistry, blood pressure, and the like. Others of the external data lines or patient care modules that connect to connectors 172 provide data relating to other aspects of patient care such data relating to feeding (e.g. volume of formula provided to the infant via a nasogastric feeding tube), data relating to the administration of intravenous fluids, data relating to waste products expelled by the infant, data related to phototherapy, electrocardiograph (EKG) data, electroencephalograph (EEG) data, and the like. Thus, connection port 170 allows data associated with devices external to device 44' to be communicated to controller 156, to computer 48', and to the hospital network. Although illustrative connection port 170 is accessible on lower portion 86 of infant platform 74, it is within the scope of this disclosure for device 44' to have a connection port located anywhere thereon, including within infant compartment 74. Device 44' has a power line 176, which receives standard 110 V, 60 Hz power from a power outlet 178 of the healthcare facility.

Controller 156 includes one or more microprocessors, microcontrollers, signal conditioning circuitry, power conditioning circuitry, memory circuitry, I/O circuitry, and the like. In some embodiments, computer 48' has its own microprocessor or microcontroller and associated circuitry that communicates with the circuitry of controller 156 via an appropriate communications protocol. In other embodiments, computer 48' is controlled by the circuitry of controller 156.

Illustrative computer 48' includes a bar code reader 178, shown in FIG. 8, to which tokens are presented to enable the bearers of the tokens to gain access to certain information. According to this disclosure, a "low access" token 180 is given to family members of the infant supported on device 44' and a "high access" token 182 is given to doctors, nurses, and other caregivers. Each token 180, 182 includes a bar code 184 that is read by reader 178. The bar code 184 associated with token 180 is different that the bar code 184 associated with token 182 so that computer 48' is able to discern which of tokens 180, 182 is being presented to reader 178. If token 182 is presented to reader 178, the bearer of token 182 has access to all of the information available via computer 48', whereas if token 180 is presented to reader 178, the bearer of token 180 is only able to access a limited amount of information via computer 48'. Tokens that grant an intermediate level of access (i.e., access to more information than is accessible with token 180, but less than is accessible with token 182) are within the scope of this disclosure.

Illustrative tokens 180, 182 are cards having bar codes 184 printed thereon or otherwise attached thereto, such as by a label, for example. It is within the scope of this disclosure for computer 48' to have readers other than bar code readers, such as magnetic strip readers, radio frequency (RF) receivers, proximity card readers, and infrared energy receivers, and for other types of associated tokens, such as cards carrying a magnetic strip, tokens that transmit a coded RF signal, a proximity card, and a token that transmits or reflects infrared energy. It is also within the scope of this disclosure for users to gain access to information by entering a user ID and password into appropriate fields appearing on display screen 118 of computer 48'.

In the description that follows, when it is stated that various data or information "appears on display screen 118" or "is displayed on screen 118" (or "appears" or "is displayed" on a portion or window of screen 118) or similar such statements, it is to be understood that the circuitry of controller 156 and/or the circuitry of computer 48' and/or circuitry in a computer device of the hospital network is executing one or more respective computer programs to cause the data or information to appear on screen 118. In addition, when it is stated that computer 48' "executes software," or "runs software," or similar such statements, to accomplish a function, such statements are intended to cover embodiments where one or more computer devices of the hospital network executes or runs the software, where controller 156 executes or runs the software, and where computer 48' itself executes or runs the software.

In the description that follows, when it is stated that an icon or button is "selected" or "highlighted" or that the user "selects" or "highlights" a button or icon or a similar such statement, it is to be understood that this disclosure is intended to cover all methods for selecting or highlighting graphical or textual images, such as icons or buttons, appearing on a computer screen. Selection of such graphical or textual images may be accomplished, for example, by moving a computer mouse to cause a cursor to overlap a portion of the image to be selected and then clicking (or double clicking) a button on the computer mouse; by using left, right, up, and down arrow keys on a computer keyboard to highlight various images and then pressing an "Enter" key of the keyboard when the desired image is highlighted; by using a "Tab" key on a computer keyboard to highlight various images and then pressing an "Enter" key of the keyboard when the desired image is highlighted; by touching a computer screen with a light pen on the portion of the screen having the desired image; using voice control software to select the desired image verbally; and, if the computer screen is a touch screen, touching the portion of the touch screen having the desired image.

Figure 9:
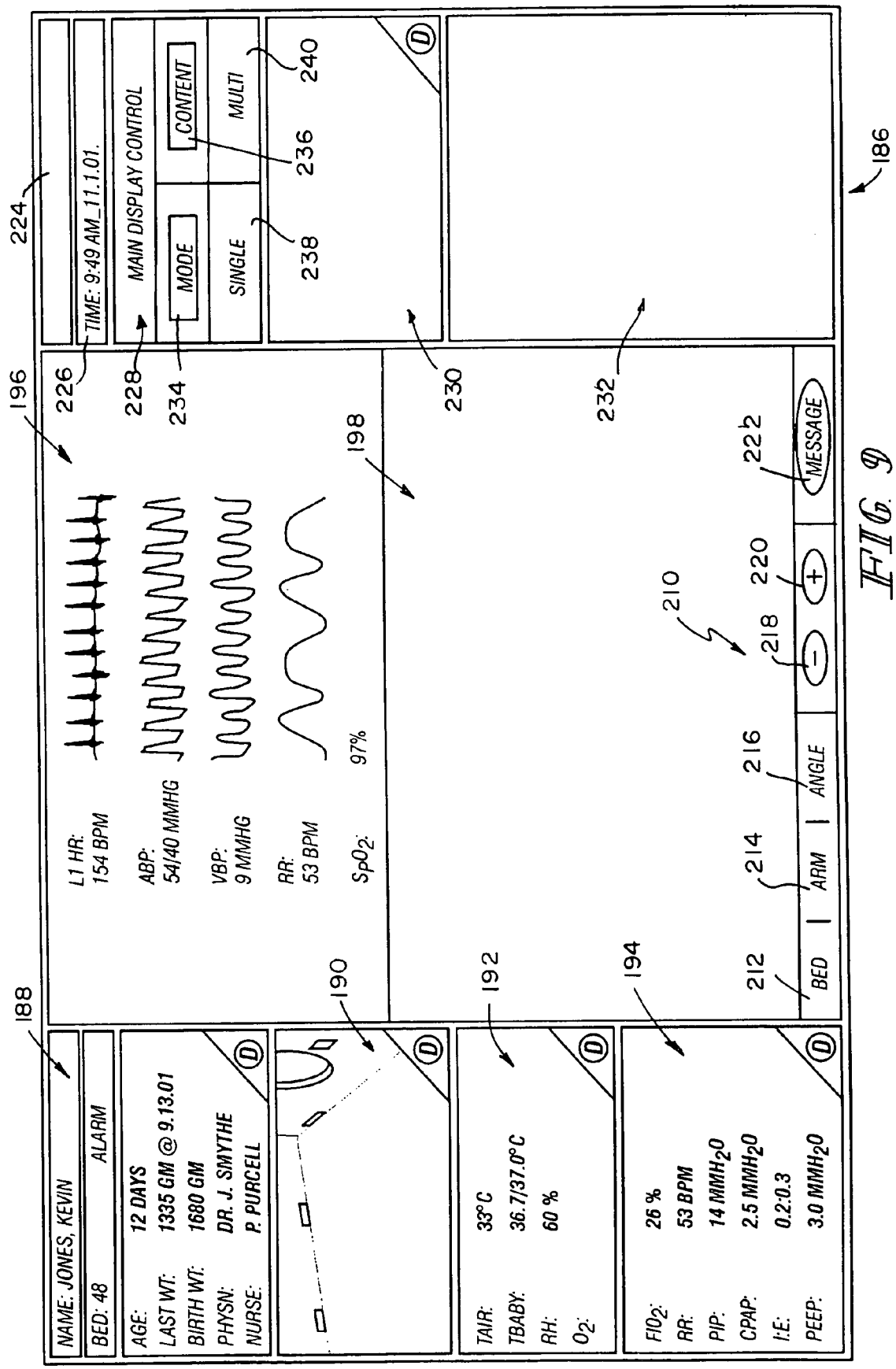
FIG. 9 is an example of a screen printout of a Default screen that appears on a display screen of the computer prior to either of the pair of tokens being presented to the reader of the computer.

Before either of tokens 180, 182 is presented to reader 178 or, if one of tokens 180, 182 has been presented to reader 178 but a predetermined period of time has elapsed without any commands being entered on computer 48', a Default screen 186 appears on display screen 118 as shown, for example, in FIG. 9. Screen 186 appears as a "split screen" display with various types of data appearing in associated windows of the split screen.

Patient biographical information is shown in a biography window 188 in an upper left region of screen 186 as shown in FIG. 9. The biographical information includes the patient's name, the bed number to which the patient is assigned, an alarm indicator (that flashes or otherwise changes state to indicate that an alarm condition has been sensed), the patient's age in days, the patient's most recent weight and the date at which the most recent weight was determined, the patient's weight at birth, the physician assigned to the patient, and the nurse assigned to the patient. Beneath window 188 is an image window 190 that displays, in realtime, the video image of the patient being captured by camera 160. Beneath window 190 is an environmental window 192 that displays environmental data, such as the temperature of the air in compartment 76, the temperature of the patient, the relative humidity in compartment 76, and the per cent oxygen concentration in compartment 76. Beneath window 192 is a vital signs data window 194 that displays vital signs data such as fraction of inspired oxygen ($FIO_2$), respiration rate (RR), peak inspiratory pressure (PIP), continuous positive airway pressure (CPAP), inspiratory/expiratory ratio (I:E:), and positive end expiratory pressure (PEEP).

In the upper, central region of screen 86, a vital signs graph window 196 is displayed on screen 186. Window 196 has graphical representations of the patient's heart rate, arterial blood pressure, venal blood pressure, and respiration rate. The patient's pulse oximetry ($SpO_2$) is also listed in window 196. Beneath window 196 is a blank window 198. Beneath window 198 is a control bar 210 having a bed icon 212, an arm icon 214, an angle icon 216, a minus-sign icon 218, a plus-sign icon 220, and a message icon 222. If a user selects icon 212, which causes icon 212 to become highlighted, and then presses either minus-sign icon 218 or plus-sign icon 220, platform 74 (and the components carried by platform 74) lowers or raises, respectively, relative to base 72. If the user selects icon 214, thereby highlighting icon 214, and then presses either minus-sign icon 218 or plus-sign icon 220, column 114 retracts or extends, respectively, relative to platform 74 to move arm 112, canopy 98, the radiant heater, and any other components coupled to any of these, downwardly or upwardly, respectively. If the user selects icon 216 and then presses either minus-sign icon 218 or plus-sign icon 220, the mattress supported by infant platform 74 is moved by associated tilting mechanisms of device 44' toward a Trendelenburg position or a reverse Trendelenburg position, respectively.

On the right hand side of screen 186 (going from the top of the screen to the bottom) are displayed a user name window 224, a time window 226, a main display control window 228, a second image window 230, and a control button window 232. Because no tokens 180, 182 have been presented to reader 178, user name window 224 and control button window 232 are blank. In some embodiments, two cameras, like camera 160, are mounted to compartment 76. In such embodiments having two cameras, second image window 230 displays the image from one of the cameras and first image window 190 displays the image from the other of the cameras. In the illustrative embodiment, windows 190, 230 sometimes display redundant images of the patient, depending upon user inputs. Thus, other types of data may sometimes be displayed in one of windows 190, 230, depending upon user inputs, and therefore, the patient's image from camera 160 is still able to be displayed in the other of windows 190, 230.

Window 228 has a "mode" button 234, a "content" button 236, a "single" button 238 and a "multi" button 240. If the user selects or highlights button 234, the user then has the option of choosing to select either button 238 or button 240. If the user selects button 238 after having first selected button 234, then data associated with the patient of the particular device 44' having computer 48' coupled thereto appears on display screen 118 as shown, for example, in FIG. 9. If the user selects button 240 after having first selected button 234, then data associated with multiple patients from multiple patient support devices 44, including device 44', appears on display screen 118 as described in further detail below with regard to FIG. 25. If a user selects button 236, then the user has the option of changing the types of data, the formatting of the data, and the arrangement of the windows containing the data that appears on the screen that the user is currently viewing. For example, if the user selects button 236 while viewing Default screen 186, then the user is able to change the information that appears on screen 186 in a desired manner. Thus, it is within the scope of this disclosure for users to customize the data appearing on each of the screens described herein. Computer 48' associates the customized screens with each of the users bearing tokens 180, 182 so that the screens are automatically configured for the particular user who presents his/her token to reader 178.

Figure 10:
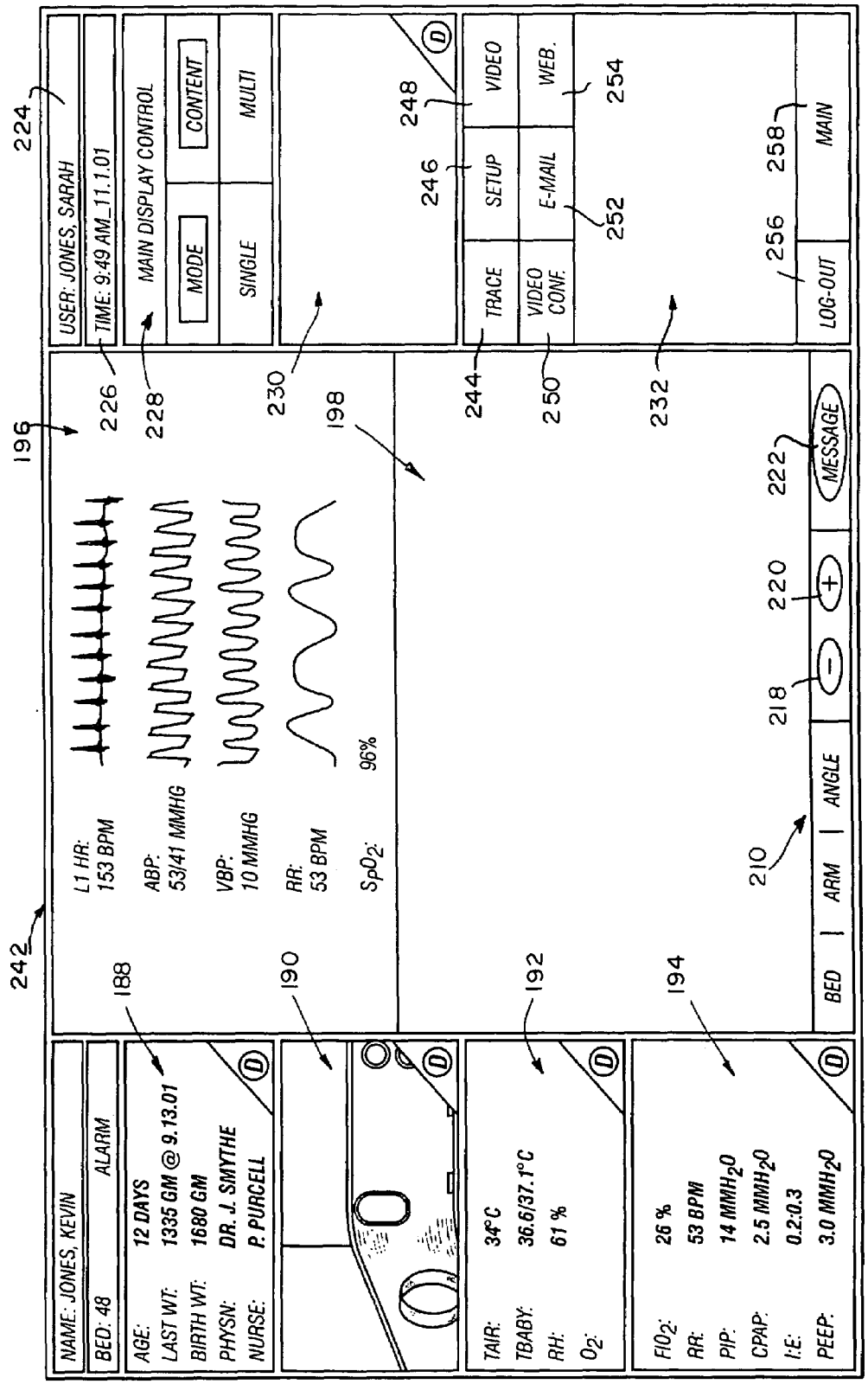
FIG. 10 is an example of a screen printout of a Low-Access Home screen that appears on the display screen when a first of the tokens of the pair of tokens, which entitles the bearer to access only a limited amount of patient point-of-care data, is presented to the reader of the computer.

After a person, such as a family member, presents "low access" token 180 to reader 178 of computer 48', a Low-Access Home screen 242 appears on display screen 118 of computer 48' as shown, for example, in FIG. 10. Screen 242 includes windows 188, 190, 192, 194, 196, 198, 226 as was the case with screen 186, although the data in each of the windows is updated substantially in realtime, as the data changes. The hospital network, computer 48', and/or controller 156 has stored therein user identification information that is associated with the particular bar code 184 on card 180. Thus, the name of the user to which card 180 has been assigned appears in window 224. In the illustrative example, Kevin Jones is the name of the patient supported on device 44' and the bearer of token 180 is Kevin's mother, Sarah Jones, as indicated by data appearing in windows 188, 224, respectively.

Window 232 of screen 242 includes a trace button 244, a setup button 246, a video button 248, a video conference button 250, an e-mail button 252, a web button 254, a log-out button 256, and a main button 258. If the user selects button 244, a screen printout of the graphs and associated information appearing in window 196 at the time button 244 is selected is printed out by a printer (not shown) that is coupled to the hospital network, controller 156, or computer 48'. If the user selects button 246, then the user is able to select images and/or data that is to be stored and/or attached to an e-mail. For example, the user has the option of capturing an image of the infant patient appearing in window 190 and e-mailing the image to a recipient, such as another family member. If the user selects button 248, computer 48' executes a software program that allows the user to leave a video message for any other person having a token for accessing data via computer 48'. The camera situated in housing 150 of computer 48' captures the video image of the user leaving the video message and a microphone that is either situated in housing 150 or that is coupled to a microphone jack 260 (FIG. 8) of computer 48' captures the audio portion of the message. It is within the scope of this disclosure for computer 48' to be programmed with any known video messaging software.

If the user selects button 250, computer 48' executes a software program that allows the user to set up or participate in a video conference. It is within the scope of this disclosure for computer 48' to be programmed with any known video conferencing software. If the user selects message icon 222, a Message screen 260 appears on display screen 118 of computer 48' as shown, for example, in FIG. 11, with a received-message table 262 and a sent-message table 264 appearing in window 198. Table 262 has one or more lines of information about any e-mails or video messages that have been sent to the user and that have not yet been viewed by the user. Table 262 has one or more lines of information about any e-mails of video messages that have been sent by the user and that have not yet been cleared or deleted by the user.

Each line item of tables 262, 264 has either a video icon 266 or an e-mail icon 268 to indicate whether the associated message is a video message or an e-mail, respectively. In addition, each line item of table 262 has a play button 267 that the user selects to play the associated video message and each line item of table 264 has a clear button 269 that the user selects to delete sent messages from table 264. Each line item of table 262 also has the name of the person that sent the message, the subject of the message, the date the message was sent to the user, and the time that the message was sent to the user. Similarly, each line item of table 264 has the name of the person to whom the user sent the message, the subject of the message, the date the message was sent by the user, and the time that the message was sent by the user.

A scroll icon 270 is provided in window 198 to the right of tables 262, 264 so that, if tables 262, 264 have more line items than are able to appear in window 198 at the same time, the user is able to scroll through the line items of tables 262, 264. At the bottom of window 198 of screen 260 are a received button 272, a sent button 274, and a new button 276. If the user wants received-message table 262 to begin at the top of window 198, the user selects received button 272 and if the user wants sent-message table 264 to begin at the top of window 198, the user selects sent button 274. If the user wants to see only the new messages that have been received, the user selects button 276.

Figure 11:
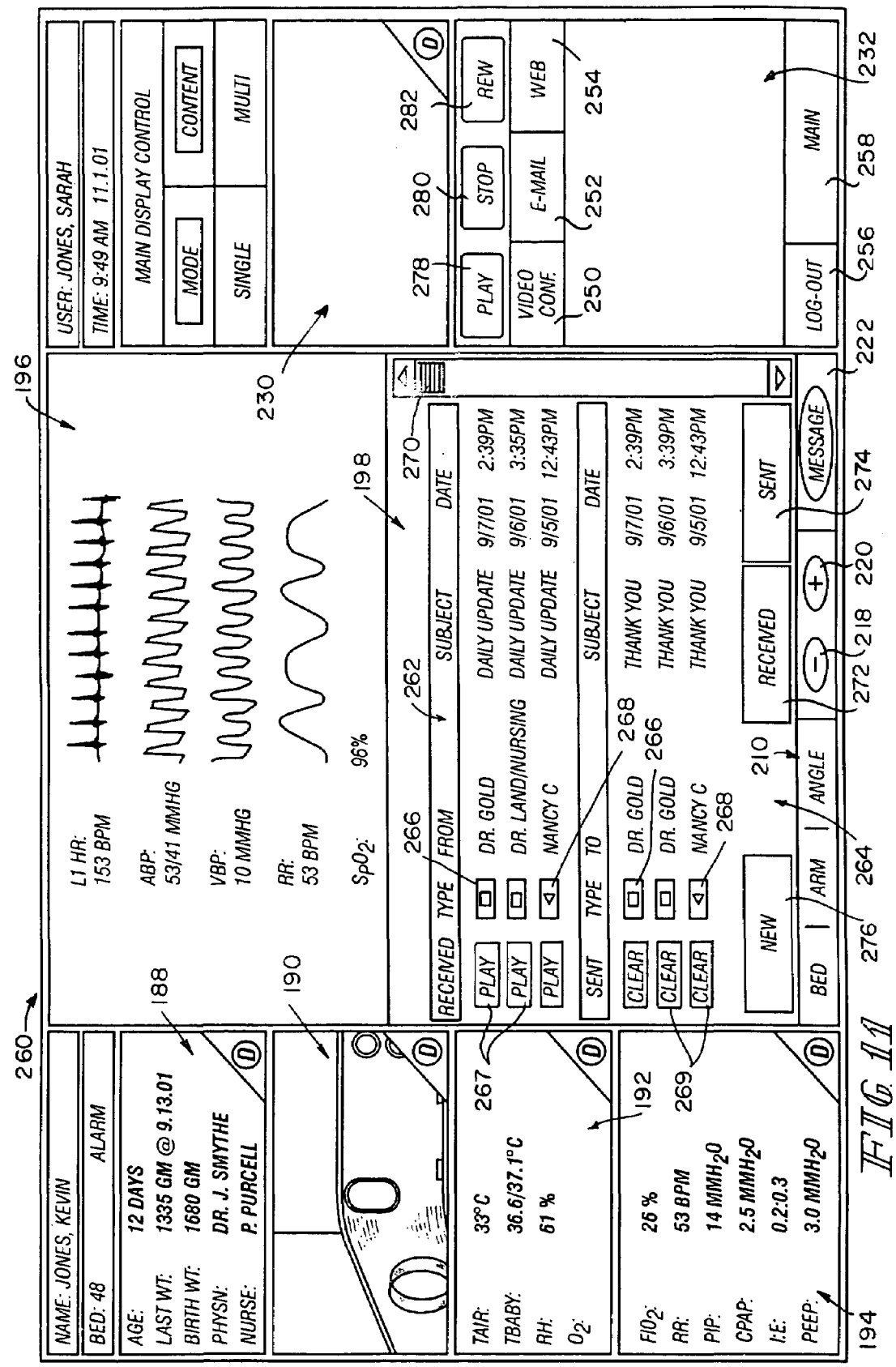
FIG. 11 is an example of a screen printout of a Message screen that appears on the display screen when a Message icon is selected on the Low-Access Home screen of FIG. 10.
Figure 12:
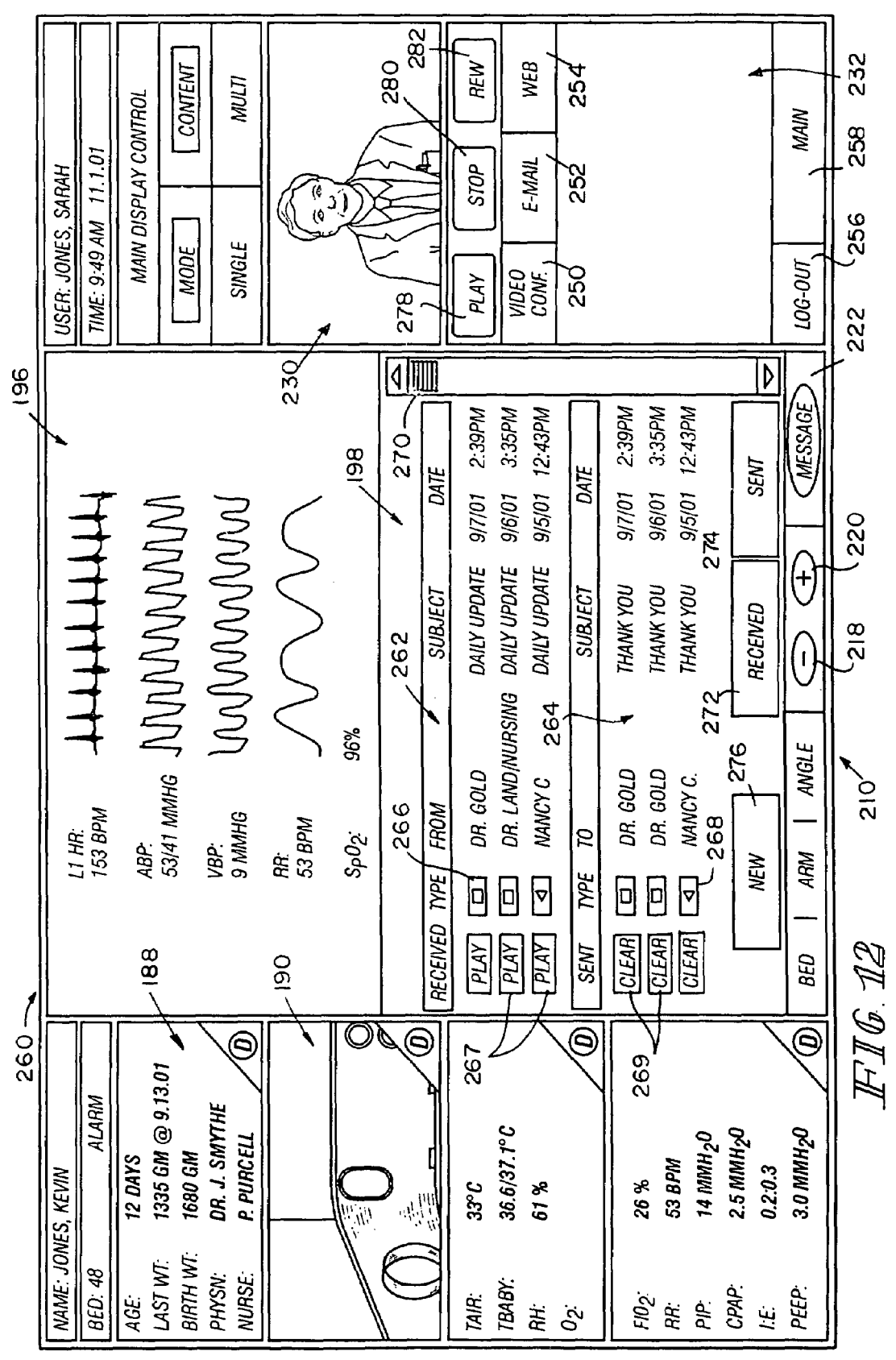

As a result of the user selecting message icon 222, the trace, setup, and video buttons 244, 246, 248 in window 232 are replaced on screen 260 with a play button 278, a stop button 280, and a rewind button 282 as shown in FIGS. 11 and 12. If the user highlights one of play buttons 267 appearing in table 262 and then selects play button 278 appearing in window 232, computer 48' plays the video message of the line item associated with the highlighted play button 267 as shown, for example in FIG. 12. While the selected video message is being played, the video data stored in memory of computer 48' is displayed in window 230 and the audio data is provided either to speakers (not shown) included in or coupled to computer 48' or to headphones (not shown) that are coupled to a headphone jack 284 (FIG. 8) of computer 48'. The user is able to adjust the volume of the audio data either by moving a volume knob 285 (FIG. 8) or by selecting icons 218, 220 of control bar 210. If the user wants to stop playing the video message, the user selects button 280. If the user wants to rewind the video message, the user selects button 282.

Figure 13:
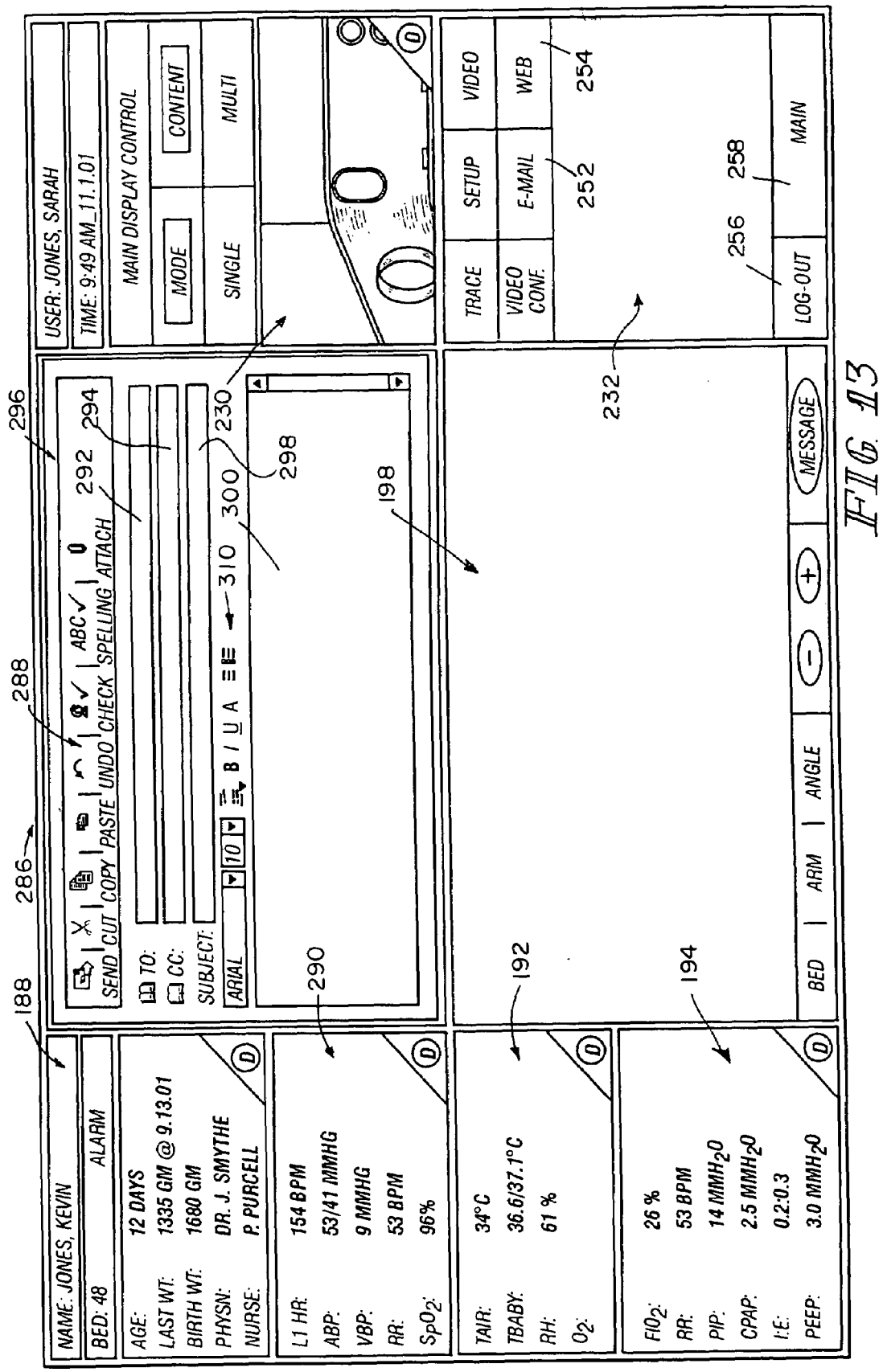
FIG. 13 is an example of a screen printout of an E-mail Control screen that appears on the display screen when an E-mail icon is selected.

If the user selects e-mail button 252 appearing in window 232 of screens 242, 260, an e-mail screen 286 appears on display screen 118 of computer 48' as shown, for example, in FIG. 13. E-mail screen 286 has an e-mail window 296 that replaces the vital signs window 196 of screens 242, 260. However, the user is still able to view vital signs data on screen 286 in substantially realtime, because image window 190 is replaced with an auxiliary vital signs window 290 containing the vital signs information, but in a tabular format instead of in a graphical format. In the illustrative embodiment, the image from camera 160 is shown in window 230 on screen 286 due to the replacement of window 190 with window 290.

E-mail window 296 has a command bar 288 including various icons that permit the user to perform a number of functions associated with composing e-mails. In the illustrative example, command bar 288 includes send, cut, copy, paste, undo, grammar check, spell check, and attach icons. The functions associated with each of these icons are commonly known. For example, using the attach icon, the user has the option of attaching any of the data and/or images that user stored memory of computer 48' using the setup button 246 as described above. Window 296 also includes a "To" dialog box 292 and a "CC" dialog box 294 in which the user types the name of the recipients of the e-mail composed by the user. Window 296 further has a "Subject" dialog box 298 in which the user types the subject of the e-mail and a message dialog box 300 in which the user types the e-mail message to be sent.

Window 296 further has a text format bar 310 which includes a number of icons and dialog boxes, such as, illustratively, a font dialog box (with an associated drop down menu arrow), a text size dialog box (with an associated drop down menu arrow), a text indent icon, a bold icon, an italicize icon, an underline icon, a text color icon, a text justification icon, and a bullet icon. The functions associated with each of these text formatting icons are commonly known. It is within the scope of this disclosure for command bar 288 and text format bar 310 to be customized to include icons that, when selected, perform associated functions. Such customization capabilities are included in commercially available e-mail software packages, such as Novell Groupwise e-mail software and Lotus Notes e-mail software.

If the user selects web button 254 appearing in window 232 of screens 242, 260, 286, for example, then a Home page (not shown) of a designated website, such as, for example, a website hosted by the hospital in which device 44' is situated or a website hosted by the manufacturer of device 44', appears in window 198. Alternatively, a web page window that overlays multiple windows appearing on screen 118 of computer 48' is displayed. Computer 48' is programmed with appropriate web browser software, such an NETSCAPE NAVIGATOR® software or MICROSOFT EXPLORER® software, that enables the user to connect to and navigate the Internet (also known as the world wide web) and that is launched when button 254 is selected. If the user selects main button 258, then computer 48' responds with screen 242, an example of which is shown in FIG. 10. If the user selects log-out button 256, then computer 48' responds with screen 186, an example of which is shown in FIG. 9.

Figure 14:
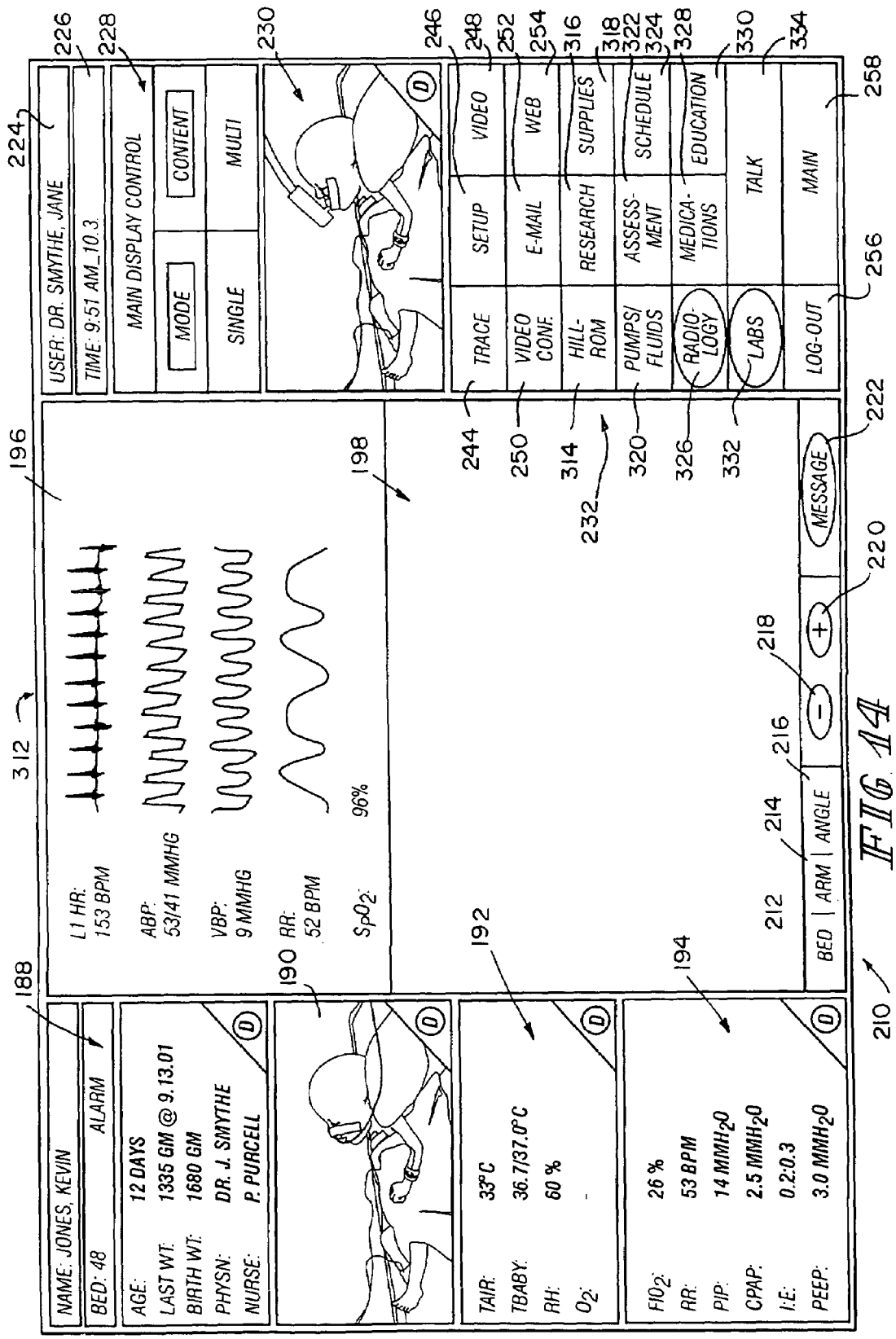
FIG. 14 is an example of a screen printout of a High-Access Home screen that appears on the display screen when a second token of the pair of tokens, which entitles the bearer to access all of the patient point-of-care data, is presented to the reader of the computer.

After a person, such as a physician or nurse, presents "high access" token 182 to reader 178 of computer 48', a High-Access Home screen 312 appears on display screen 118 of computer 48' as shown, for example, in FIG. 14. Screen 312 includes windows 188, 190, 192, 194, 196, 198, 226 as was the case with screen 186, although the data in each of the windows is updated substantially in realtime, as the data changes. The hospital network, computer 48', and/or controller 156 has stored therein user identification information that is associated with the particular bar code 184 on card 182. Thus, the name of the user to which card 182 has been assigned appears in window 224. In the illustrative example, the bearer of token 182 is Kevin Jones' physician, Dr. Jane Smythe, as indicated by data appearing in window 224.

As was the case with window 232 of screen 242, window 232 of screen 312 includes trace button 244, setup button 246, video button 248, video conference button 250, e-mail button 252, web button 254, log-out button 256, and main button 258. However, window 232 of screen 312 also includes a sales/service button 314, a research button 316, a supplies button 318, a pumps/fluids button 320, an assessment button 322, a schedule button 324, a radiology button 326, a medications button 328, an education button 330, a labs button 332, and a talk button 334 as shown in FIG. 14. Selection of buttons 244, 246, 248, 252, 254, 256, 258 on screen 312 or on any other screen accessible from High-Access Home screen 312 results in substantially similar screens and data appearing on display screen 118 of computer 48' as was described above with reference to FIGS. 10–13. Screen 312 also has icons 212, 214, 216, 218, 220, 222, the selection of which retrieves similar data and/or performs similar functions for each of these respective buttons as was described above with reference to FIGS. 9–13, although the message tables that appear in window 198 of screen 312 when icon 222 is selected include line items that correspond to messages that were received by or sent by the bearer of token 182 rather than the bearer of token 180.

Figure 15:
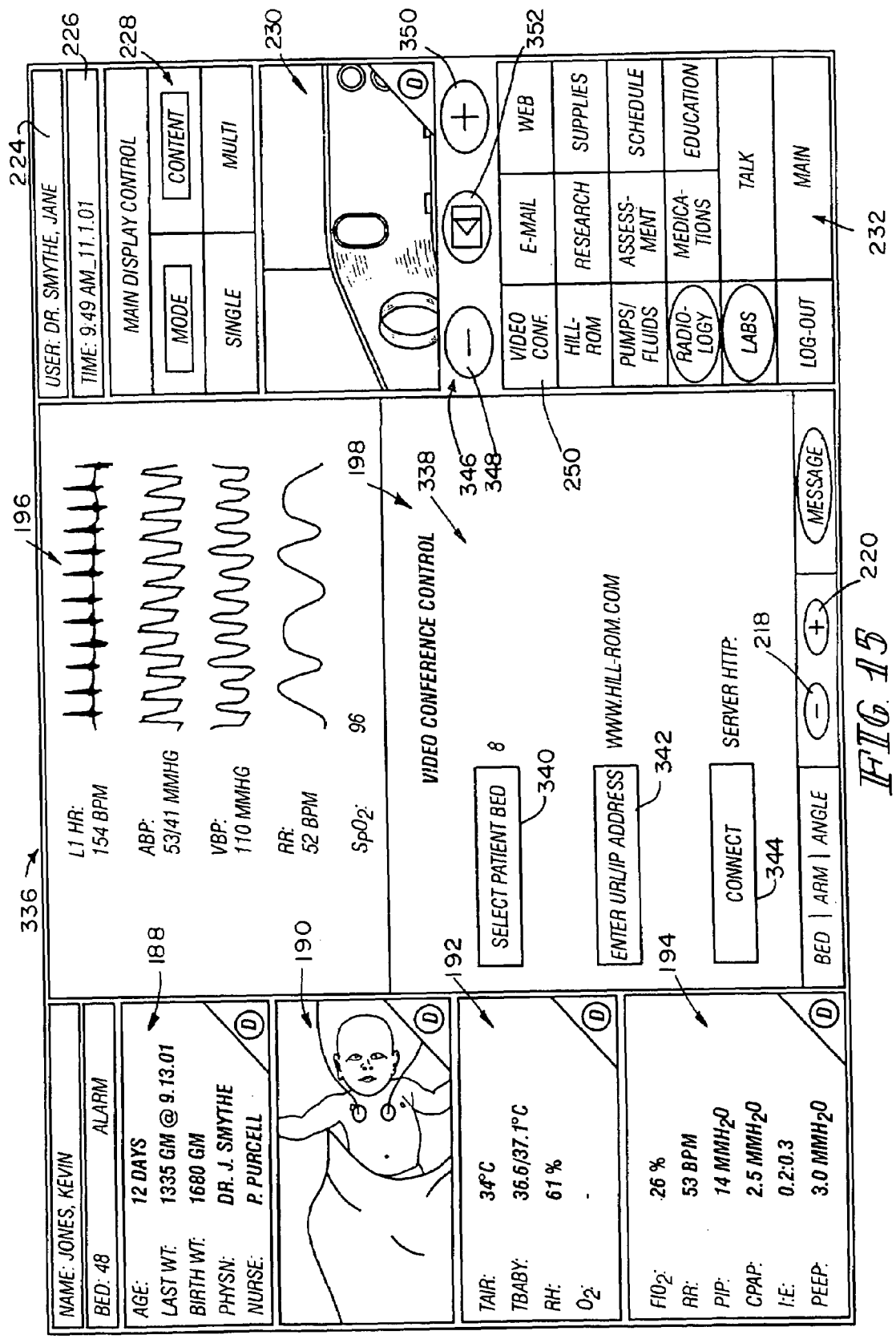
FIG. 15 is an example of a screen printout of a Video Conference Control screen that appears on the display screen when a Video Conf. icon is selected from a main menu associated with the High-Access Home screen.

If the user selects video conference icon 250, a video conference control screen 336 appears on display screen 118 of computer 48' as shown, for example, in FIG. 15. Window 198 of screen 336 has a video conference control panel 338 which includes a "select patient bed" button 340, an "enter URL/IP address" button 342, and a "connect" button 344. After the user selects button 340 on screen 336, the user is able to identify which device 44 is to have the associated images available on the video conference. The default patient bed, in this example, is device 44'. However, the user has the option of selecting any of the patient beds (i.e. devices 44) that are coupled to the hospital network. After the user selects button 342, the user is able to identify the other party or parties to the video conference by their Internet address or addresses. After the user has identified the patient bed and the recipients to be included in the video conference, the user selects button 344 to connect to the recipient. Thus, according to this disclosure, video conferencing is accomplished via the world wide web. However, it is within the scope of this disclosure for computer 48' to be programmed with any known video-conferencing software, including software that permits videoconferencing via a LAN, a WAN, or via direct line communication.

When the user selects button 250, thereby causing screen 336 to appear on the display screen 118 of computer 48', the trace, setup, and video buttons 244, 246, 248 are replaced with a camera-control bar 346 which, in the exemplary embodiment, includes a zoom-out button 348, a zoom-in button 350, and a change-camera button 352. It is within the scope of this disclosure for any one or more of the cameras of device 44', including the camera in housing 150 of computer 48' and camera 160 mounted to compartment 76, to be motorized and for camera-control bar 346 to include buttons for panning the cameras to the right and to the left, for moving the cameras up and down, and for controlling the brightness or tint or any other parameter associated with a video camera.

By selecting button 352, the user is able to switch the image that appears in window 230, which image is typically an image from a camera of one of the other parties to the videoconference. Thus, by successive selections of button 352, the user is able to see, in a serial fashion, the images from each of the cameras associated with the other parties to the videoconference and is also able to see the images associated with camera 160 and with the camera in housing 150 of computer 48'. By selecting button 348, the user is able to zoom in on the image appearing in window 230 and by selecting button 350, the user is able to zoom out on the image appearing in window. Thus, if the image appearing in window 230 is an image from a camera associated with one of the other parties to the videoconference, then computer 48' generates the appropriate signals to control the camera of that other party, assuming that the camera of the other party is configured to be controlled by signals generated by computer 48'.

In some embodiments, the user controls the image that is transmitted to the other parties to the videoconference. In such embodiments, the image available to the other parties to the videoconference is shown in window 230. Also in such embodiments, successive selections of button 352 results in the image shown in window 230 toggling between the image associated with camera 160 and the image associated with the camera in housing 150 (and with any other camera of device 44') and, in addition, buttons 348, 350 are selected to zoom out or zoom in, respectively, on the image appearing in window 230. During the videoconference, volume knob 285 or, alternatively, icons 218, 220 are used to adjust the volume of the audio portion of the conference.

Figure 16:
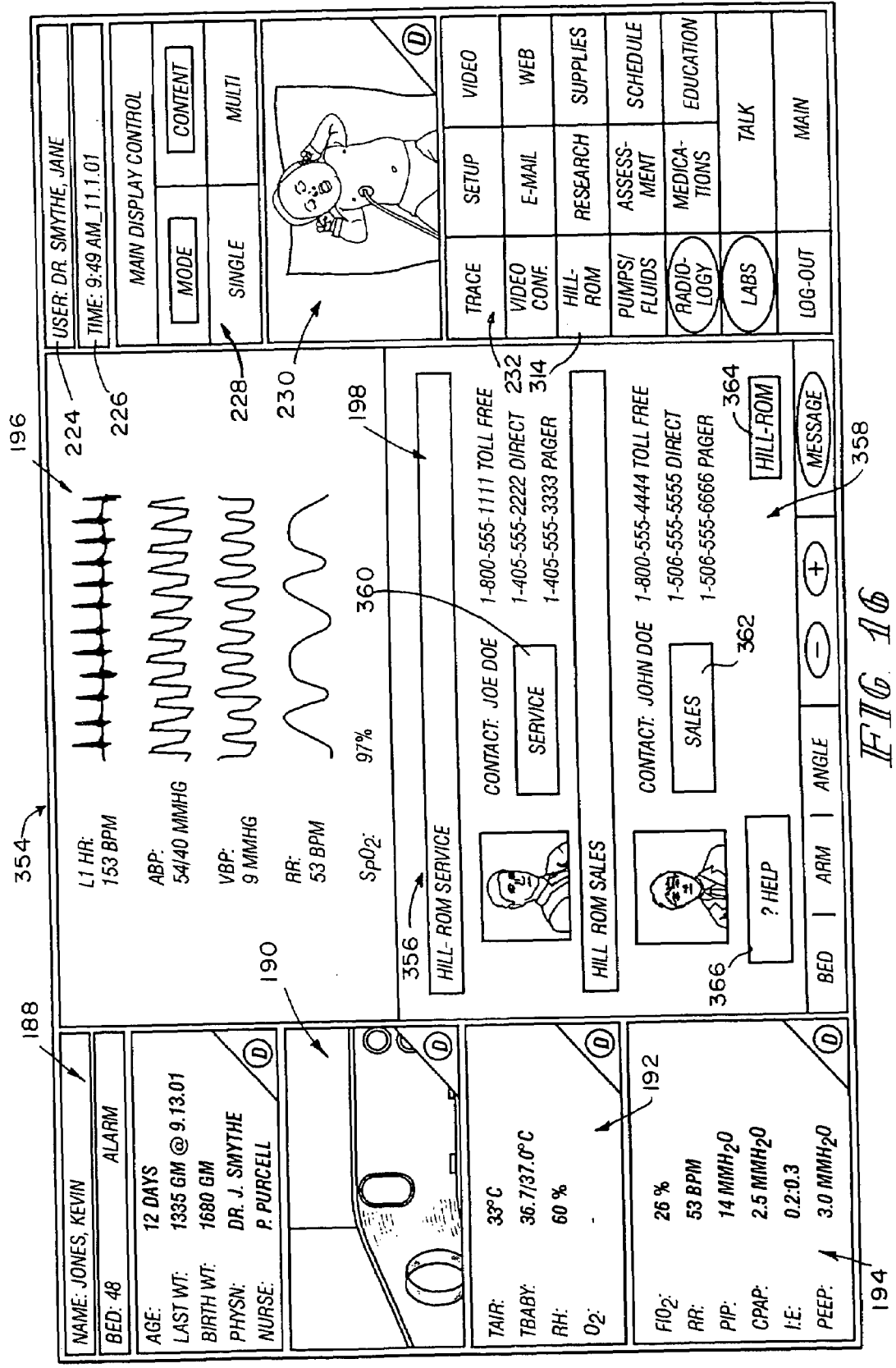
FIG. 16 is an example of a screen printout of a Sales & Service screen that appears on the display screen when a Sales & Service icon is selected from the main menu.

If the user selects sales/service button 314 in window 232, a Sales & Service screen 354 appears on display screen 118 of computer 48' as shown, for example, in FIG. 16. Window 198 of screen 354 has a service-contact table 356 and a sales-contact table 358. Table 356 includes service contact information, such as a picture of a customer service representative or technician assigned to the hospital associated with device 44', the name of the customer service representative or technician, and the phone numbers at which the customer service representative or technician can be reached. In addition, table 356 has a service icon 360 that, when selected, causes e-mail screen 286 to appear on display 118 with the e-mail address of the customer service representative or technician already typed into dialog box 292 so that the user can compose and send an e-mail message to request service information or to request a visit by the customer service representative or technician.

Table 358 includes sales contact information, such as a picture of a sales representative assigned to the hospital associated with device 44', the name of the sales representative, and the phone numbers at which the sales representative can be reached. In addition, table 358 has a sales icon 362 that, when selected, causes email screen 286 to appear on display 118 with the e-mail address of the sales representative already typed into dialog box 292 so that the user can compose and send an e-mail message to request sales information or to request a visit by the sales representative. Table 358 also has a manufacturer web-link icon 364 that, when selected, causes a Home page of a website of the manufacturer of device 44' to appear on display screen 118 of computer 48'. In the illustrative example, button 314 and icon 364 each have "Hill-Rom" appearing thereon to indicate that Hill-Rom is the manufacturer of device 44'. Alternatively, button 314 has other text thereon, such as "Sales & Service" or "Mfg. Contact", and icon 354 has other text thereon, such as "Mfg. Home Page" or "Link to Mfg. Website," for example. Table 358 further has a help icon 366 that, when selected, links the user to a help program of computer 48'. Using the help program, the user is able to type queries or look up information regarding the operation of device 44'.

Figure 17:
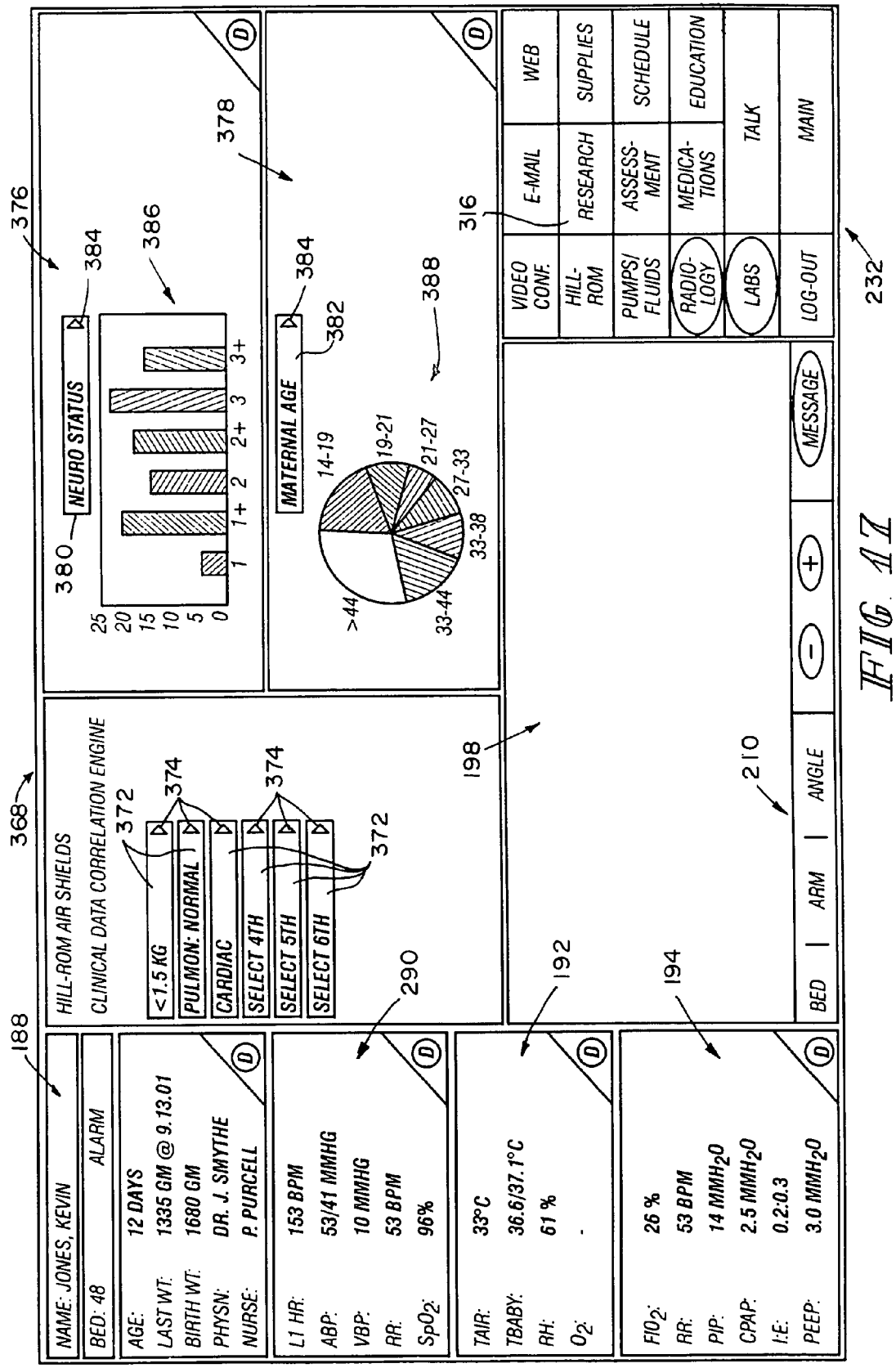
FIG. 17 is an example of a screen printout of a Research screen that appears on the display screen when a Research icon is selected from the main menu.

If the user selects research button 316, a Research screen 368 appears on display screen 118 of computer 48' as shown, for example, in FIG. 17. Illustrative screen 368 includes a correlation-parameter window 370, a first research data window 376, and a second research data window 378. Windows 370, 376, 378 replace some of the windows, or portions thereof, that appeared on display screen 118 prior to the selection of button 316. For example, vital signs graph window 196 is replaced by windows 370, 376, 378. However, the user is still able to view vital signs data on screen 386 in substantially realtime, because image window 190 is replaced with auxiliary vital signs window 290, which contains the vital signs information, but in a tabular format instead of in a graphical format.

It is within the scope of this disclosure for any of the data accessible from any portion of any of the patient point-of-care data management systems described herein, including systems 10, 100, 200, to be sorted, assimilated, mined, graphed, tabulated, correlated and the like and to be presented to the user on research screen 368. In the illustrative example, window 370 includes a set of six parameter entry icons 372, each having a menu arrow 374. To select the parameters to be correlated, the user selects an arrow 374 of a respective icon 372 to cause an associated menu of parameter choices to appear on screen 368. The user, then selects one of the parameters from the menu of parameter choices. This selection of parameters is repeated until the user has selected the desired number of parameters (up to six in the illustrative example).

Based on the selected parameters, certain data from databases included in the network or system, of which device 44' is a part, is provided to computer 48' for display in windows 376, 378 of screen 368. Window 376 has a first research results icon 380 and window 378 has a second research results icon 382 as shown in FIG. 17. Each of icons 380, 382 has associated therewith a respective next arrow 384. By successively selecting either of icons 380, 382, the user is able to scroll through the available research data. In alternative embodiments, selecting icons 380, 382 causes an associated drop down menu of available research-data choices to appear in the respective window 376, 378 and then the user is able to select from the menu, the desired research data to be displayed in the corresponding window 376, 378.

In the illustrative example of FIG. 17, "Neuro Status" is depicted in icon 380 and an associated bar graph 386 (e.g., a Brazleton assessment) appears in window 376. Also in the illustrative example, "Maternal Age" is depicted in icon 382 and an associated pie chart 388 appears in window 378. In some embodiments, the research data displayed in windows 376, 378 is based on realtime patient point-of-care data of the various patients from which systems 10, 100, 200 are receiving data currently. In other embodiments, the data shown in windows 376, 378 is based on historical patient point-of-care data of the various patients from which systems 10, 100, 200 received data in the past. In still other embodiments, the research data appearing in windows 376, 378 is based on data received from some other source or that is entered into systems 10, 100, 200 manually. It is within the scope of this disclosure for the research data accessible via computer 48' to be based on an aggregation or combination of data from any of the above described sources of data.

Figure 18:
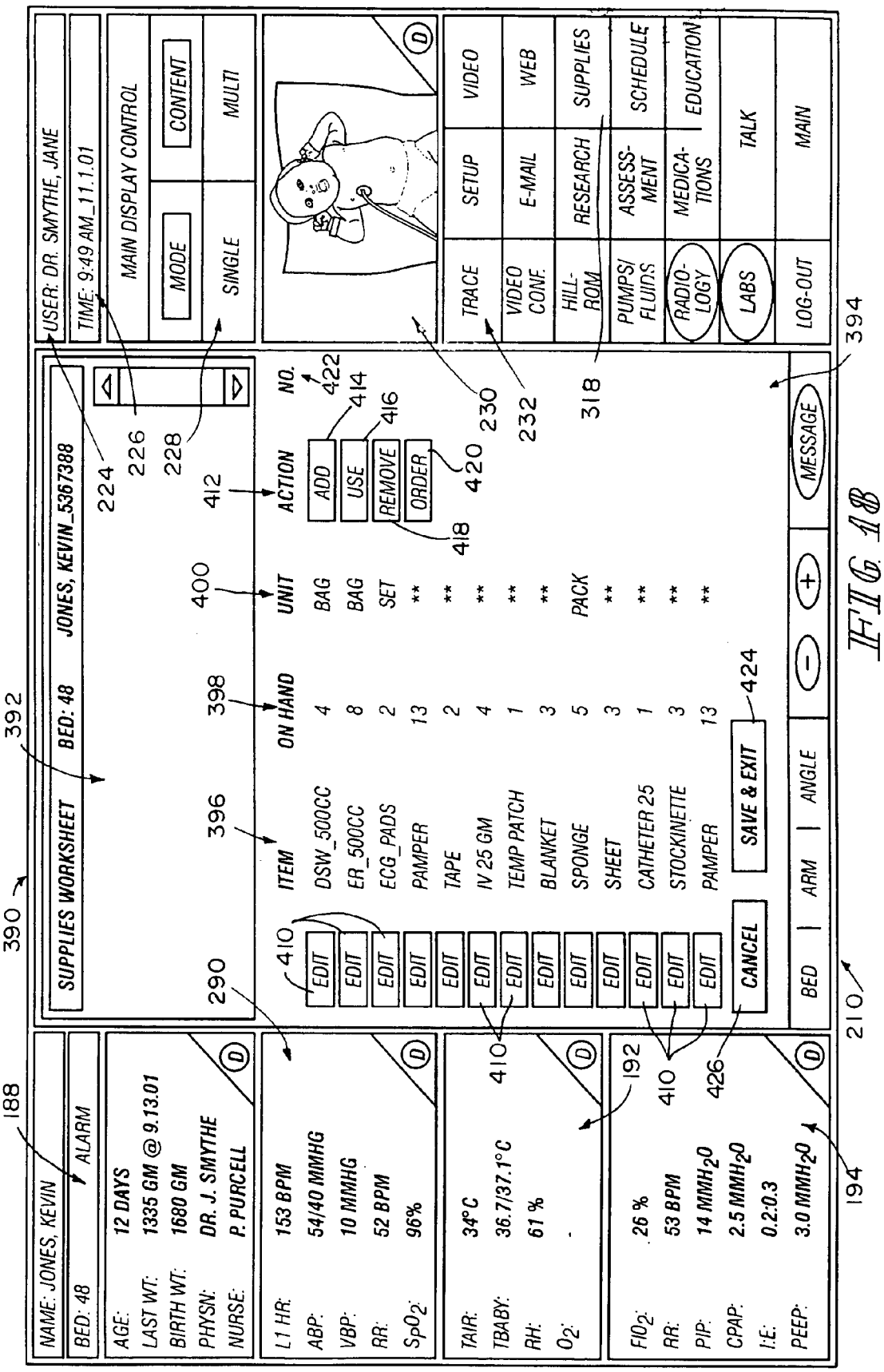
FIG. 18 is an example of a screen printout of a Supplies screen that appears on the display screen when a Supplies icon is selected from the main menu.

If the user selects supplies button 318 from menu 232, a Supplies screen 390 appears on display screen 118 of computer 48' as shown, for example, in FIG. 18. Illustrative screen 390 includes a supplies worksheet window 392 and a supplies list window 394. Windows 392, 394 replace windows 196, 198, which appeared on display screen 18 prior to the selection of button 318. As a result, data from vital signs graph window 196 is shown in a tabular format and in substantially realtime in auxiliary vital signs window 290, which replaces window 190. In addition, the image from camera 160 is shown in window 230 on screen 390 due to the replacement of window 190 with window 290.

Window 394 of screen 390 has a list of the supplies that are available by the infant and/or that are available in storage compartments on or near device 44'. The list of supplies appearing in window 394 includes an item column 396 that shows the name of the associated supply, an "on hand" column 398 that shows the number of units of the item that are available, and a unit column 400 that shows the type of unit (e.g. bag, set, pack, bottle) if appropriate. The list of supplies in window 394 in the illustrative example includes four bags of dextrose in saline solution (D5W 500CC solution), eight bags of ER 500CC intravenous solution, two sets of ECG pads, thirteen pampers, two rolls of tape, four 25 gram IV's, one temperature patch, three blankets, five packs of sponges, three sheets, one catheter 25, three stockinettes, and an additional thirteen pampers. It is within the scope of this disclosure for any type of supply used to care for a patient may be included on the list of supplies.

Window 394 has a plurality of edit icons 410, each of which is situated alongside a respective supply item listed in window 394 as shown in FIG. 18. Window 394 also has an action column 412 which includes an add icon 414, a use icon 416, a remove icon 418, and an order icon 420. After the user selects a particular supply line item, by selecting the associated icon 410, the user is then able to select the appropriate one of icons 414, 416, 418, 420 to perform the desired action. For example, the user selects icon 414 to add one or more items to the selected line item and the user selects icon 416 if the user is going to use one or more items of the selected line item. In addition, the user selects icon 418 if the user wants to remove one or more items from the selected line item, but is otherwise not going to use the removed items. Selecting icon 416 causes the system associated with device 44' to bill the patient for the use of the selected item, whereas if icon 418 is selected, the system associated with device 44' does not bill the patient. Selection of icon 418 is appropriate, for example, if the selected supply is going to be used for another patient or is going to be returned to a supply room of the hospital. Selecting icon 420 enables the user to order more of the selected item from the supply room of the hospital.

Whenever one of icons 414, 416, 418, 420 is selected, a number dialog box (not shown) appears in a number column 422 alongside the selected one of icons 414, 416, 418, 420. The user then types into the number dialog box, the quantity of units of the selected supply that the user wants to add, use, remove, or order, as the case may be. If none of edit icons 410 are selected prior to the user selecting either icon 414 or icon 420, then selection of either of icons 414, 420 causes window 392 to become active thereby enabling the user to type in the information about the supply to be added to window 394 or to be ordered, as the case may be. Window 394 further has a Save & Exit icon 424 that the user selects after editing window 394 and/or entering information in window 392. Selecting icon 424 causes the information appearing in columns 396, 398, 400 to be updated automatically. Window 394 has a cancel icon 426 that the user selects if the user wants to undo any of the changes that the user has made to windows 392, 394.

Figure 19:
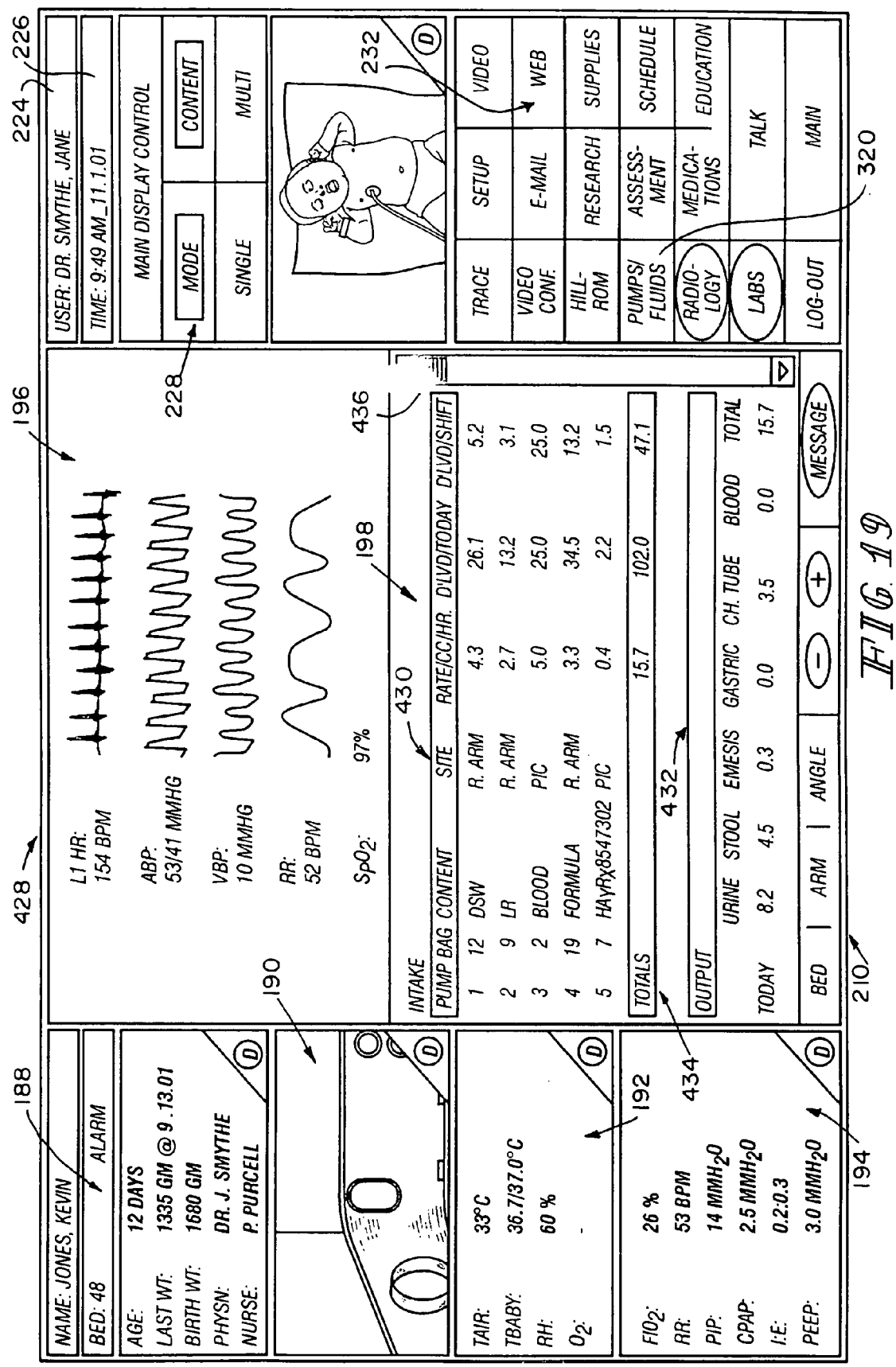
FIG. 19 is an example of a screen printout of a Pumps/Fluids screen that appears on the display screen when a Pumps/Fluids icon is selected from the main menu.

If the user selects button 320 in window 232, a Pumps/Fluids screen 428 appears on display screen 118 of computer 48' as shown, for example, in FIG. 19. Window 198 of screen 428 has an intake table 430 and an output table 432. Intake table 430 lists various types of information relating to the fluids being infused, pumped, or otherwise delivered to the patient. Each line item in illustrative table 430 provides the following information: the number of the pump causing the associated fluid to be administered to the patient, the number of the bag of the associated fluid, the contents of the associated bag, the site on the patient at which the fluid is being administered, the rate in cubic centimeters per hour at which the fluid is being administered to the patient, the amount of fluid delivered to the patient during the current day, and the amount of fluid delivered to the patient during the current shift. In addition, table 430 has a "totals" row 434 in which is shown the sum of the rates at which all of the fluids are being administered to the patient, the sum of the amount of all of the fluids delivered to the patient during the current day, and the sum of the amount of all of the fluids delivered to the patient during the current shift. Output table 432 lists the volume rates (in cubic centimeters per hour) at which fluids of various types are being expelled from the patient. Table 432 also lists the sum total of the fluids being expelled from the patient.

In the illustrative example, the fluids shown in table 430 as being delivered to the patient include dextrose in saline solution (DSW), lactated ringers solution (LR), blood, formula, and $HA_{Y}R_{X}8547302$. However, it is within the scope of this disclosure for any type of fluid that may be used in the healthcare environment for treating a patient to be included in table 430. In the illustrative example, the fluids shown in table 432 as being output by the patient include urine, stool, emesis (e.g., vomit), gastric fluid, chest tube fluid, and blood. It is within the scope of this disclosure for other types of patient fluids to be shown in table 432. A scroll icon 436 is provided alongside tables 430, 432, if needed, to permit the user to scroll through all of the entries appearing in tables 430, 432.

Figure 20:
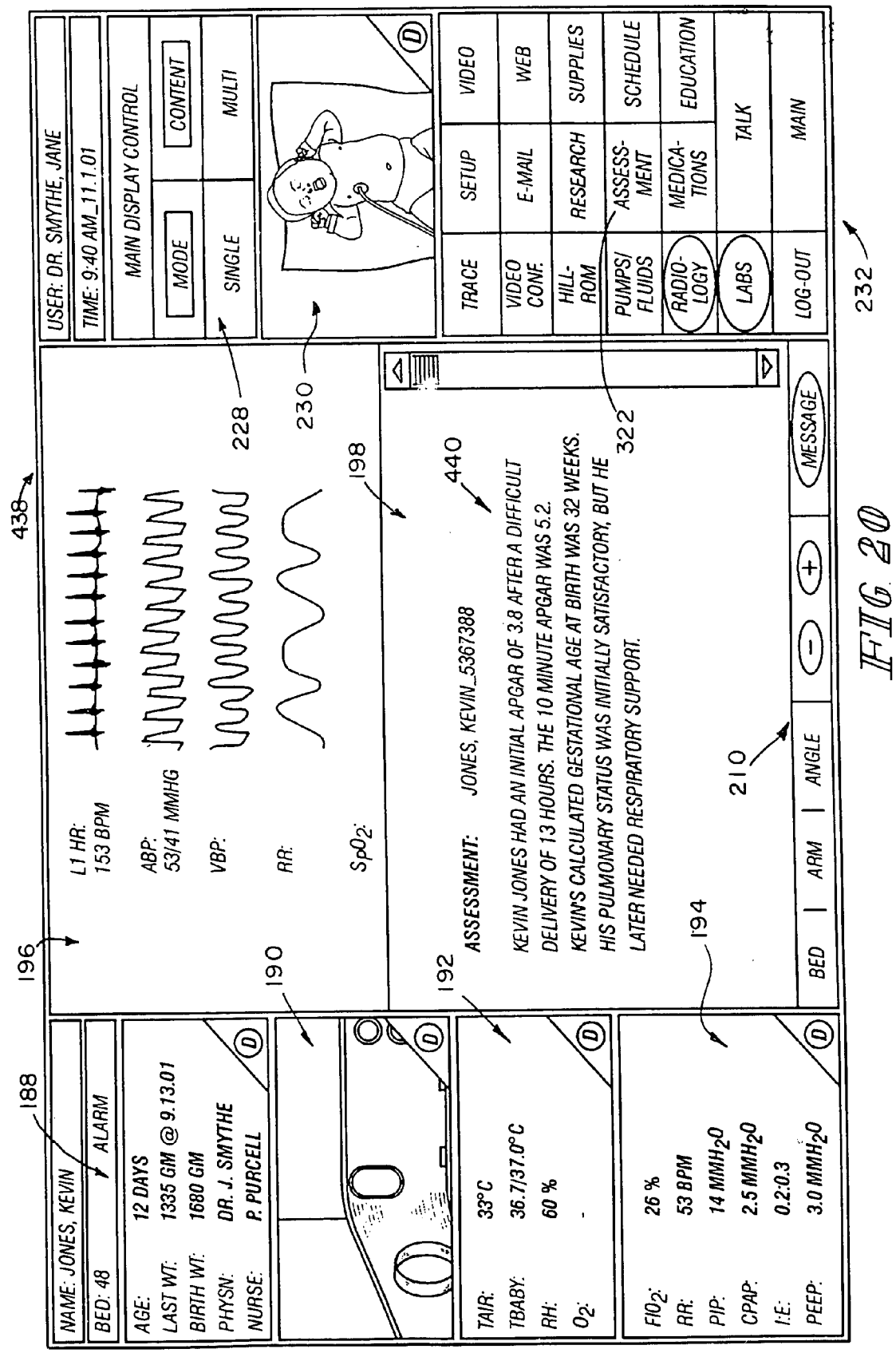
FIG. 20 is an example of a screen printout of an Assessment screen that appears on the display screen when an Assessment icon is selected from the main menu.

If the user selects button 322 on control button menu 232, an Assessment screen 438 appears on display screen 118 of computer 48' as shown, for example, in FIG. 20. Window 198 of screen 438 has a block of text 440 that indicates the physician's assessment of the patient. In the illustrative example, block of text 440 indicates that the patient had an initial APGAR (i.e., a score based on an infant's activity, pulse, grimace, appearance, and respiration) of 3.8 after a difficult delivery of thirteen hours; that the ten minute APGAR was 5.2; that the patient's calculated gestational age at birth was thirty two weeks; and that the patient's pulmonary status was initially satisfactory, but later the patient needed respiratory support. However, it will be appreciated that the type of information and statements that a physician or caregiver may include in any particular assessment is practically limitless. Text 440 either is entered manually on keyboard 144 of computer 48' or is accessed by computer 48' from another computer device included the system and having the assessment stored therein.

Figure 21:
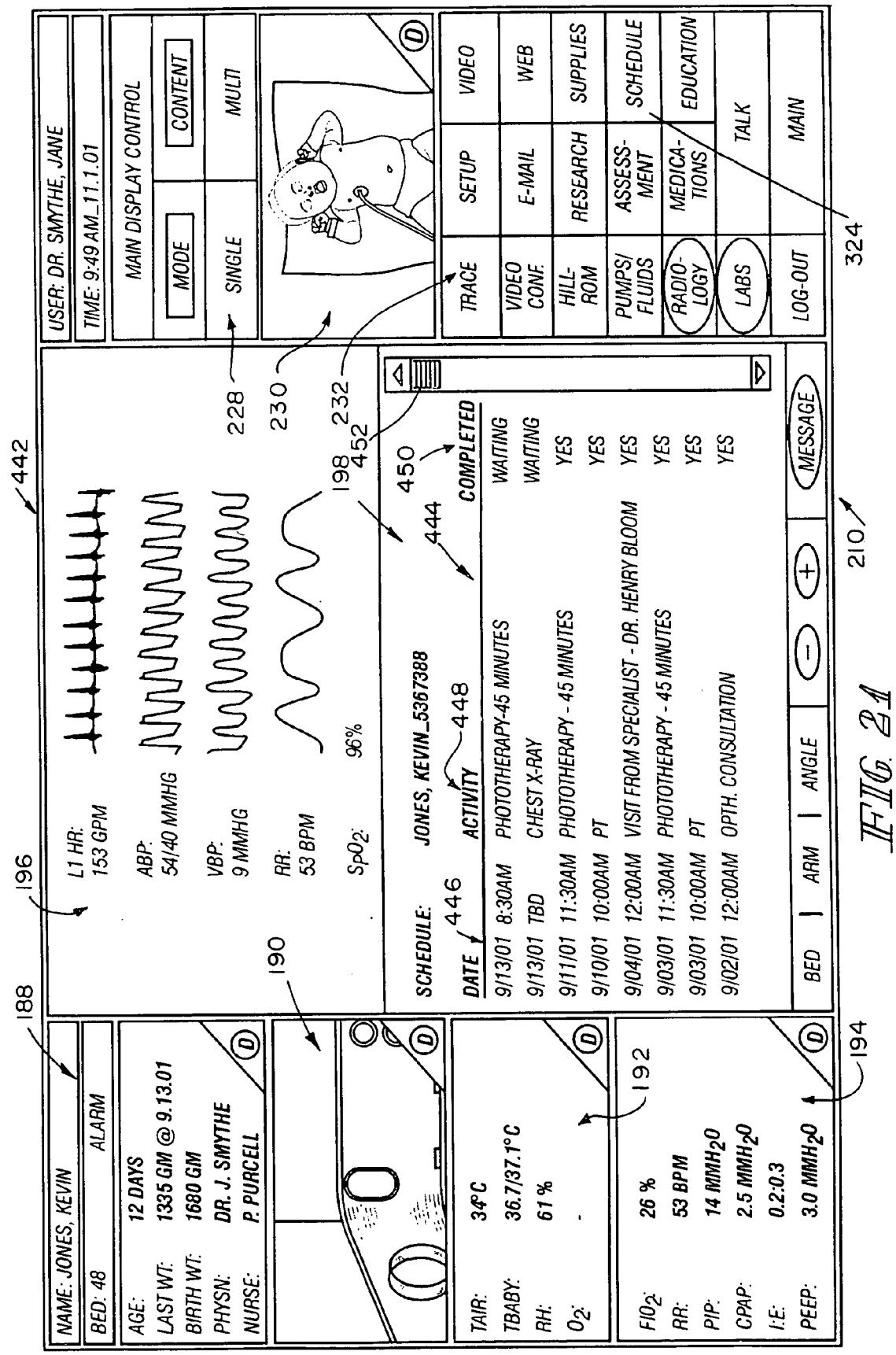
FIG. 21 is an example of a screen printout of a Schedule screen that appears on the display screen when a Schedule icon is selected from the main menu.

If the user selects button 324 on control button menu 232, a Schedule screen 442 appears on display screen 118 of computer 48' as shown, for example, in FIG. 21. Window 198 of screen 442 has a schedule table 444 which, in turn, has a date & time column 446, an activity column 448, and a completed column 450. The information in column 446 indicates the date and time at which a scheduled activity either is to take place or has taken place. The information in column 448 briefly describes the activity to take place or the activity that has taken place. The information in column 450 indicates whether the activity has taken place or whether the activity has not yet taken place. In the illustrative example the activities listed in table 444 include a number of forty five minute phototherapy sessions, a chest X-ray, a number of physical therapy (PT) sessions, and an ophthalmologic consultation. It is within the scope of this disclosure for any type of activity to be included in table 444. In the illustrative example, the word "waiting" in a line item indicates the associated activity has not yet taken place and the word "yes" in a line item indicates that the associated activity has taken place. A scroll icon 452 is provided alongside table 444, if necessary, to permit the user to scroll through the activities listed in table 444.

Figure 22:
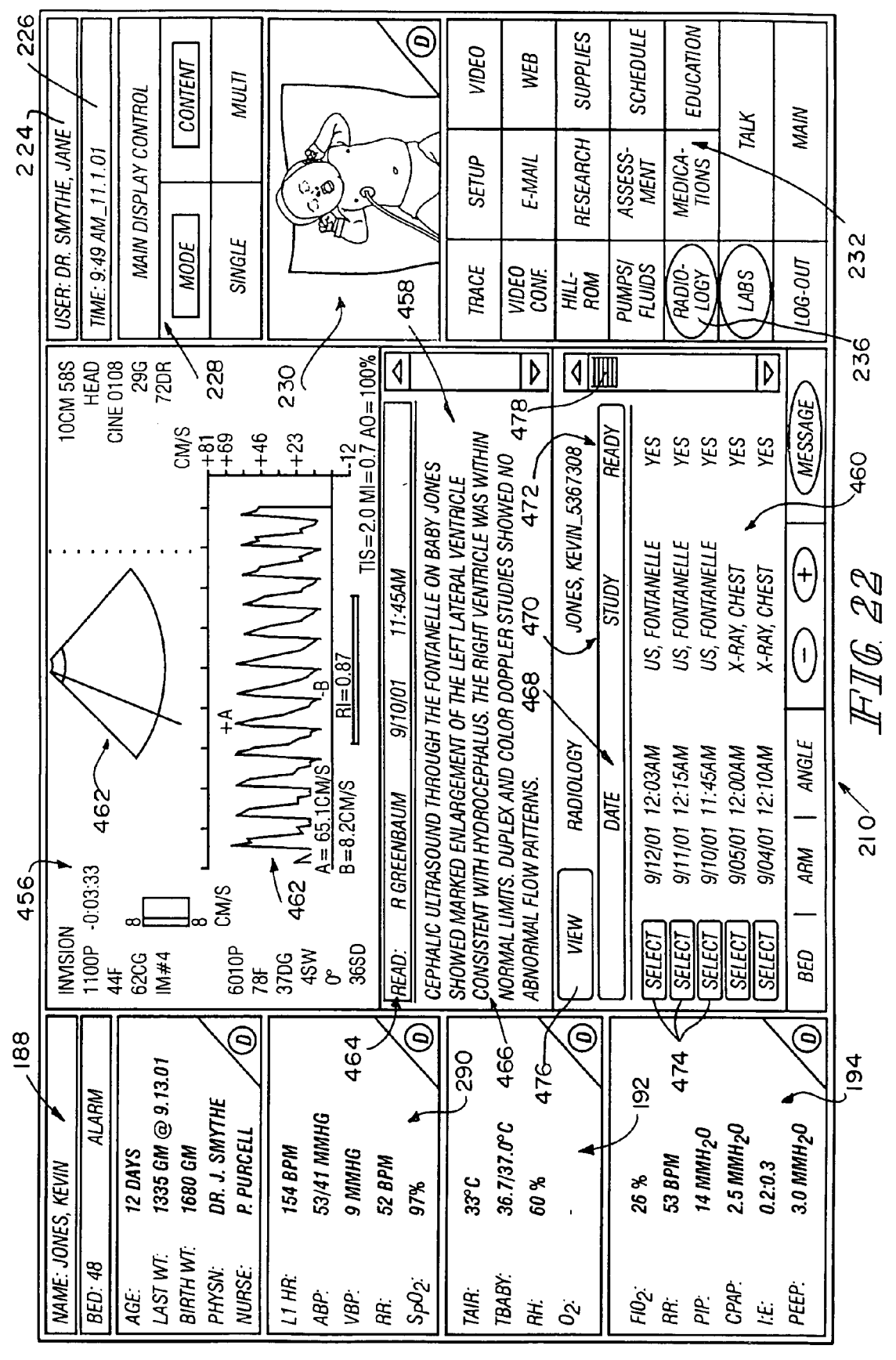

If the user selects button 326 on control button menu 232, a Radiology screen 454 appears on display screen 118 of computer 48' as shown, for example, in FIG. 22. Screen 454 has a radiology image window 456, a radiology assessment window 458, and a radiology selection table 460. Window 456 has one or more radiology images 462 and any accompanying data provided with the image(s). Images 462 include, for example, ultrasound images and/or x-ray images. Window 458 includes a line of information 464 that indicates the name of the person who read the images and the date and time that the images were read. Window 458 also has a block of text 466 that provides an assessment of the patient based on the images appearing in window 456. In the illustrative example, text 464 indicates that the images are a cephalic ultrasound through the fontanelle of the patient, the ultrasound showed marked enlargement of the left lateral ventricle consistent with hydrocephalus, that the right ventricle was within normal limits, and that duplex and color Doppler studies showed no abnormal flow patterns. It will be appreciated that the type of information and statements that a physician or caregiver may include in any particular assessment appearing in window 458 is practically limitless. The images and data appearing in windows 456, 458, 460 is stored in memory devices of computer 48', controller 156, or any other computer device included in the associated system.

Table 468 includes a date & time column 468, a study column 470, and a ready column 472 as shown in FIG. 22. The date and time that the associated radiology image was taken is listed in column 468. The information in column 470 briefly describes the type of radiology images of the respective line items in table 468. The information in column 472 indicates whether the radiology image is ready for viewing or whether the radiology image is still being processed. In the illustrative example, the types of radiology images listed in column 470 include a number of ultrasound (US), fontanelle images and a number of X-ray, chest images. Also in the illustrative example, the word "yes" appears in column 472 for each line item to indicate that each of the associated radiology images is ready for viewing.

Table 468 includes a plurality of "select" icons 474, each of which is situated alongside a respective line item listed of table 460 as shown in FIG. 22. The user selects the desired icon 474 and then selects a view icon 476 in order to view in window 456 a particular radiology image or images 462 associated with the selected icon 474 and to view the associated assessment 466 in window 458. A scroll icon 478 appears alongside table 460, if needed, to permit the user to scroll through all of the entries in table 460. A similar scroll icon (not shown) is provided alongside assessment 466, if needed.

If the user selects button 328 on control button menu 232, a Medications screen 480 appears on display screen 118 of computer 48' as shown, for example, in FIG. 23. Window 198 of screen 480 has a medications table 482 that has a drug column 484, a supplied column 486, a dose/kg column 488, a dose (mg) column 490, and a dose (ml) column 492. The names of the drugs prescribed to the patient are listed in column 484. In the illustrative example, atropine, NAHCO₃, calcium glucomate, dextroxe (10%), epinepherine 1:10,000, Lasix, and Lidocaine (2%) appear in column 484. However, it is within the scope of this disclosure for any type of medication that is prescribed to a patient to be included on table 482. For each drug listed in column 484, column 486 shows the amount supplied, column 488 shows the dose per kilogram, column 490 shows the dose in milligrams, and column 492 shows the dose in milliliters. Computer 48' automatically calculates the doses shown in column 490 by multiplying the patient's weight by the associated number appearing in column 488. In addition, computer 48' automatically calculates the doses shown in column 492 by dividing the numbers appearing in column 486 into the respective numbers appearing in column 490.

Table 482 includes a change weight icon 494, an edit needs icon 496, a get info icon 498, and a details icon 500 as shown in FIG. 23. If the user selects icon 494, the user is able to change the weight of the patient which, in turn, causes computer 48' to automatically adjust the dose numbers appearing in columns 490 and 492 based on the new weight. If the user selects icon 496, the user is able to add a drug to table 482 or delete a drug from table 482. If the user selects icon 498, the user is able to obtain information about the drugs that may be administered to the patient. If the user selects icon 500, the user is able to obtain other types of information, such as information about interpreting the data that appears in table 482 and historical data about the drugs and doses of drugs administered to the patient in the past.

If the user selects button 330 from control button menu 232, the user is able to link to various education modules (not shown). The education modules may be stored in computer devices of the hospital network or they may be accessible on the internet. In some embodiments, the education modules are linked to or associated with an organization that is able to grant continuing education credits for the completion of various education modules. Thus, after selecting button 330, the user is able to launch an education module, read education materials associated with the module, and then take a test electronically. If the user passes the test, then continuing education credits are given to the user. It is contemplated by this disclosure that a user may use computer 48' to complete only a portion of an education module during a first session and that the user may use computer 48' to complete the education module during a second, later session.

Figure 24:
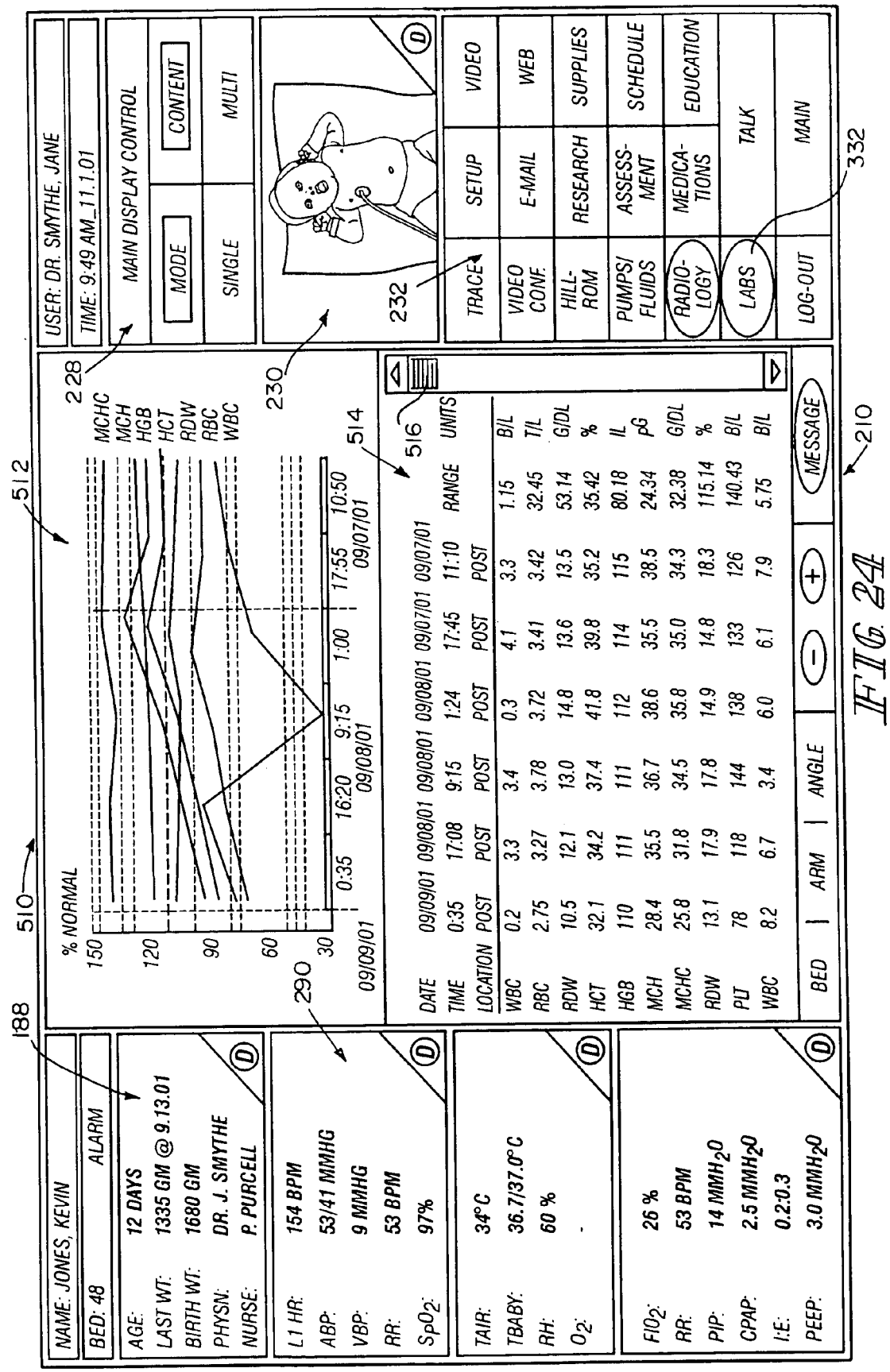
FIG. 24 is an example of a screen printout of a Labs screen that appears on the display screen when a Labs icon is selected from the main menu.

If the user selects button 332 from control button menu 232, a Labs screen 510 appears on display screen 118 of computer 48' as shown, for example, in FIG. 24. Screen 510 includes a labs graph 512 and a labs table 514. Illustrative graph 512 and table 514 relate to laboratory test results of the patient's blood. Included in graph 512 and table 514 is information about the patient's white blood count (WBC), red blood count (RBC), red cell distribution width (RDW), hematocrit (HCT), hemoglobin (HGB), mean corpuscular hemoglobin (MCH), mean corpuscular hemoglobin concentration (MCHC), and platelettes (PLT). However, it is within the scope of this disclosure for laboratory test results of all types and in all formats to be displayed on screen 510. The laboratory test results are stored in any of the computer devices of the system or network to which device 44' is a part and are accessible to computer 48' for viewing.

Graph 512 shows the date and time that the various blood samples were taken from the patient. Table 514 also shows the date and time that the various blood samples were taken from the patient, but table 514 further shows the location in the hospital where the samples were taken, the range of each line item in table 514, and the units associated with each line item in table 514. The y-axis of graph 512 is per cent normal and ranges between thirty per cent and one hundred fifty percent. The data in table 514, in many instances, is the actual blood test readings for a particular characteristic of the blood sample in the respective units specified. A scroll icon 516 appears alongside table 514, if necessary, to permit the user to scroll up and down table 514 to view all of the information included therein.

Computer 48' is able to function as a communication device of a nurse call system. Nurse call systems are discussed in more detail in U.S. Pat. Nos. 6,362,725; 5,822,544; 5,838,223; 5,689,229; 5,561,412; 5,594,786; 4,967,195; and 4,601,064; each of which is hereby incorporated by reference herein. If the user selects Talk button 334 from control button menu 232, then the user is able to respond to a "call" placed by a remote user of the nurse call system. To respond to the call, the user of computer 48' speaks into a microphone housed in computer 48' or a microphone coupled to microphone jack 261 to communicate with the remote user. In addition, the audio from the remote user is heard by the user of computer 48' through speakers included in computer 48' or through headphones coupled to headphone jack 284.

Figure 25:
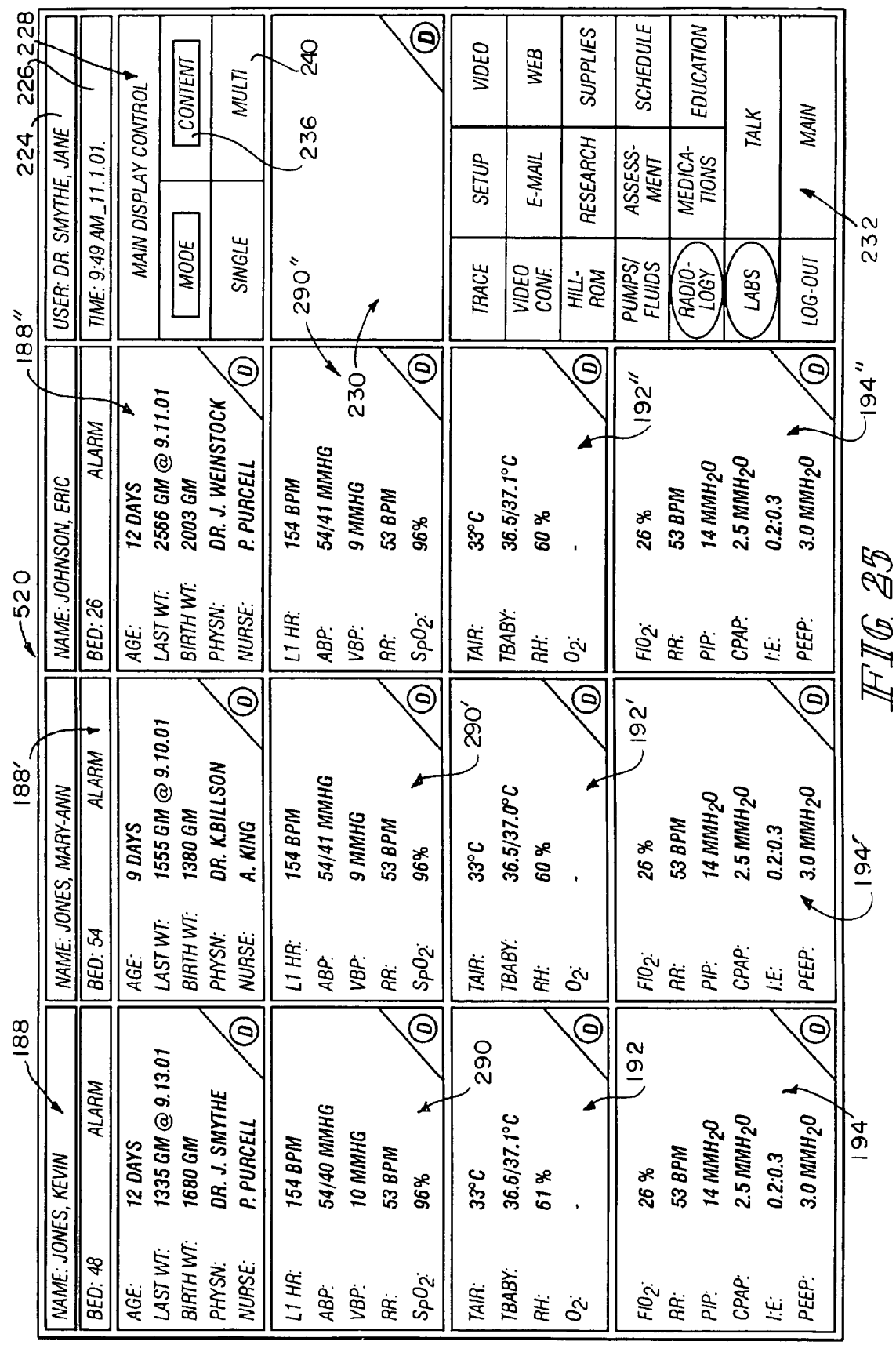
FIG. 25 is an example of a screen printout of a Multi-Mode screen that appears on the display screen when a Multi icon is selected.

If the user associated with card 182 selects multi button 240 of window 228, a Multi-Device screen 520 appears on display screen 118 of computer 48' as shown in, for example, in FIG. 25. Screen 520 has a first column of information, including windows 188, 192, 194, 290 that are associated with a first patient; a second column of information, including windows 188', 192', 194', 290' that are associated with a second patient; and a third column of information, including windows 188", 192", 194", 290" that are associated with a third patient. Windows 224, 226, 228, 230, 232 also appear on screen 520.

The description above of the types of data shown in windows 188, 192, 194, 290 is applicable to windows 188', 188", 192', 192", 194', 194", 290', 290" as well. Thus, patient point-of-care data of multiple patients is viewable simultaneously on display screen 118 of computer 48'. In some embodiments, if the user selects any portion of the first, second, or third columns having data associated with first, second, and third patients, respectively, the image from the camera 160 aimed at the respective patient is displayed in window 230. In addition, if the user selects content button 236 after having selected button 240, the user is able to change the patients from which data is acquired, the types of data shown for each patient, the formatting of the data, and the arrangement of the windows containing the data that appears on screen 520. It is within the scope of this disclosure for patient point-of-care data from more than three patients or less than three patients to be shown on screen 520.

The description above of the various types of patient point-of-care data that appear on the various screens shown in FIGS. 9–25 is not to be construed as limiting this disclosure to only those types of data shown. In accordance with this disclosure, patient point-of-care data of all types may be displayed on display screen 118 of computer 48' in one or more windows. In addition, although much of the patient point-of-care data described herein is acquired in realtime or in substantially realtime, it is within the scope of this disclosure for historical patient point-of-care data for one or more patients to be displayed on display screen 118 of computer 48'.

Although the apparatus and method for patient point-of-care data management has been described in detail with reference to certain preferred embodiments, variations and modifications exist within the scope and spirit of this disclosure as described and defined in the following claims.

The invention claimed is:

1. An integrated patient care device comprising:
   a support structure adapted to support a patient thereon,
   a computer system coupled to said support structure,
   a display screen mounted adjacent said support structure,
   a first camera coupled to said support structure and directed at the patient on said support structure,
   a second camera located adjacent said display screen,
   a sound recording means,
   a sound reproducing means, and
   a storage means,
   said first camera being coupled to said computer system and arranged to capture a first image of the patient under control of said computer system,
   said second camera being coupled to said computer system and arranged to capture a second image of a patient care giver or other person authorized to have access to said patient care device when authorized by said computer system,
   said second image being arranged to be stored in said storage means,
   said sound recording means being arranged to record information-bearing sounds from said patient care giver or other person when authorized by said computer system,
   said display screen being selectively operative to selectively display said first image on a first portion of said display screen and patient point-of-care data on a second portion of said display screen, said display screen being selectively operative when authorized by said computer system to display said second image on a portion of said display screen and to cause said sound reproducing means to reproduce said information-bearing sounds,
   said computer system being arranged to provide authorization for various functions of said device in response to appropriate input signals provided to said computer system.

2. The patient care device of claim 1, wherein the computer system is configured to permit the images from the cameras to be accessible via the Internet for viewing on a display screen of a remote computer.

3. The patient care device of claim 1, wherein the computer system is configured to permit the images from the cameras to be e-mailed to an e-mail address.

4. The patient care device of claim 1, wherein the display screen has a third portion on which is shown environmental data that is indicative of an environmental condition in a patient space near the support structure.

5. The patient care device of claim 1, wherein the display screen has a third portion on which is shown patient biographical data.

6. The patient care device of claim 1, wherein the display screen has a third portion on which is shown a stored radiology image of the patient.

7. The patient care device of claim 1, wherein the display screen has a third portion on which is shown a stored ultrasound image of the patient.

8. The patient care device of claim 1, wherein the display screen has a third portion on which is shown stored laboratory test results.

9. The patient care device of claim 1, wherein the display screen has a third portion on which is shown a recorded video message.

10. The patient care device of claim 1, wherein the display screen has a third portion on which is shown controls for listening to a recorded audio message.

11. The patient care device of claim 1, wherein the display screen has a third portion on which is shown controls for sending an e-mail.

12. The patient care device of claim 1, wherein the display screen has a third portion on which is shown controls for conducting a videoconference.

13. The patient care device of claim 1, wherein the display screen has third portion on which is shown controls for browsing the Internet.

14. The patient care device of claim 1, wherein the display screen has a third portion on which is shown a list of supplies associated with the care of the patient.

15. The patient care device of claim 1, wherein the display screen has a third portion on which is shown a schedule of medical appointments of the patient.

16. The patient care device of claim 1, wherein the display screen has a third portion on which is shown data pertaining to medications associated with the patient.

17. The patient care device of claim 1, wherein the display screen has a third portion on which is shown additional point-of-care data associated with at least one other patient supported on at least one other patient care device.

18. An infant support apparatus comprising a base, an infant support platform coupled to the base and configured to support an infant, a canopy positioned above the infant support platform, an infant compartment in which the infant is situated being defined between the canopy and the infant support platform, a first video camera aimed toward the infant to provide a first video image of the infant, a second camera coupled to the infant support platform and arranged to capture a second image of a care giver or other person authorized to have access to the infant support apparatus, a patient sensor sensing at least one physiological condition of the infant, and a data management system comprising a computer, a display screen mounted adjacent said support structure, sound recording means, sound reproducing means, and storage means, said data management system being arranged for receiving from said first video camera said first video image and receiving from said sensor data indicative of said at least one physiological condition, said data management system being arranged to capture said second image and store said second image in said storage means when authorized by said data management system, said sound recording means being arranged to record information-bearing sounds from said patient care giver or other person when authorized by said data management system, said display screen being selectively operative to selectively display said first video image on a first portion of said display screen and simultaneously display the data indicative of said at least one physiological condition of the infant, said display screen also being selectively operative when authorized by said data management system to display said second image on said display screen and to cause said sound reproducing means to reproduce said information-bearing sounds, said data management system being arranged to provide authorization for various functions in response to appropriate input signals provided thereto.

19. The infant support apparatus of claim 18, further comprising an environmental sensor sensing at least one environmental condition in the infant compartment, the data management system receiving from the environmental sensor data indicative of the at least one environmental condition, and the display screen displaying the data indicative of the at least one environmental condition simultaneously with the video at least one of the video images and the data indicative of the at least one physiological condition of the infant.

20. The infant support apparatus of claim 18, wherein the computer is supported with respect to the infant support platform and the computer comprises the display screen.

21. The infant support apparatus of claim 20, further comprising an arm assembly extending from the infant support platform, the computer being coupled to the arm assembly, and the arm assembly being movable to permit repositioning of the computer relative to the infant support platform.

\* \* \* \* \*